United States Patent
Tal et al.

(10) Patent No.: US 8,662,081 B2
(45) Date of Patent: *Mar. 4, 2014

(54) INTRAUTERINE DEVICE

(75) Inventors: Michael G. Tal, Woodbridge, CT (US);
Patrick N. Gutelius, Monroe, CT (US);
Mark J. DeBisschop, Burlington, CT (US); Oleg Shikhman, Trumbull, CT (US); Pasquale Patrizio, Guilford, CT (US)

(73) Assignees: Yale University, New Haven, CT (US); Contramed LLC, Charlotte, NC (US)

(*) Notice: Subject to any disclaimer, the term of this patent is extended or adjusted under 35 U.S.C. 154(b) by 402 days.

This patent is subject to a terminal disclaimer.

(21) Appl. No.: 12/856,876

(22) Filed: Aug. 16, 2010

(65) Prior Publication Data
US 2010/0300452 A1    Dec. 2, 2010

Related U.S. Application Data

(63) Continuation-in-part of application No. 12/353,770, filed on Jan. 14, 2009, now Pat. No. 8,181,653, and a continuation-in-part of application No. 11/892,560, filed on Aug. 23, 2007, now Pat. No. 7,621,276, which is a continuation-in-part of application No. 11/884,027, filed as application No. PCT/US2006/005245 on Feb. 15, 2006, now Pat. No. 7,669,601.

(60) Provisional application No. 61/006,454, filed on Jan. 15, 2008, provisional application No. 60/653,743, filed on Feb. 15, 2005.

(51) Int. Cl.
*A61F 6/06* (2006.01)

(52) U.S. Cl.
USPC ............ 128/833; 128/830; 128/831; 128/840

(58) Field of Classification Search
USPC .................................................. 128/830–840
See application file for complete search history.

(56) References Cited

U.S. PATENT DOCUMENTS

| | | | |
|---|---|---|---|
| 3,374,788 A | 3/1968 | Rosenthal | |
| 3,405,711 A | 10/1968 | Bakunin | |

(Continued)

FOREIGN PATENT DOCUMENTS

| | | |
|---|---|---|
| CH | 688984 | 7/1998 |
| DE | 4412311 | 10/1995 |

(Continued)

OTHER PUBLICATIONS

Valle, Tissue response to the STOP microcoil transcervical permane contraceptive device:results from a prehysterectomy study, Fertility and Sterility, V. 76, Iss. 5, Nov. 2001.

*Primary Examiner* — Kim M Lewis
(74) *Attorney, Agent, or Firm* — Welsh Flaxman & Gitler LLC

(57) ABSTRACT

An intrauterine device for applying pressure to the walls of the uterine cavity includes a resilient body having an elongated member which includes a first end and a second end which are resiliently biased away from each other. The first end of the elongated member includes a first leg having a first end and a second end. The second end of the elongated member includes a second leg having a first end and a second end. A connection member is positioned between the first end of the first leg and the first end of the second leg. A first plug member is secured at the second end of the first leg and a second plug member is secured at the first end of the second leg. The first and second plug members are shaped and dimensioned for bearing against the walls of the uterine cavity as the elongated member spreads outwardly with the first end and the second end moving apart. A method for preventing conception within the uterine cavity is also disclosed.

38 Claims, 28 Drawing Sheets

(56) References Cited

U.S. PATENT DOCUMENTS

| | | | |
|---|---|---|---|
| 3,507,274 A | 4/1970 | Soichet | |
| 3,620,212 A | 11/1971 | Fannon, Jr. et al. | |
| 3,659,596 A | 5/1972 | Robinson | |
| 3,678,927 A * | 7/1972 | Soichet | 128/840 |
| 3,683,905 A | 8/1972 | Chaft | |
| 3,683,906 A | 8/1972 | Robinson | |
| 3,687,129 A | 8/1972 | Nuwayser | |
| 3,704,704 A | 12/1972 | Gonzales | |
| 3,789,838 A | 2/1974 | Fournier et al. | |
| 3,805,767 A | 4/1974 | Erb | |
| 3,811,435 A | 5/1974 | Soichet | |
| 3,845,761 A | 11/1974 | Zaffaroni | |
| 3,918,443 A | 11/1975 | Vennard et al. | |
| 4,034,749 A * | 7/1977 | Von Kesseru et al. | 128/833 |
| 4,117,839 A | 10/1978 | Morris | |
| 4,353,363 A | 10/1982 | Sopena Quesada | |
| 4,537,186 A | 8/1985 | Verschoof et al. | |
| 4,612,924 A | 9/1986 | Cimber | |
| 4,628,924 A | 12/1986 | Cimber | |
| 4,932,421 A | 6/1990 | Kaali et al. | |
| 5,095,917 A | 3/1992 | Vancaillie | |
| 5,146,931 A | 9/1992 | Kurz | |
| 5,555,896 A | 9/1996 | Cimber | |
| 5,935,137 A | 8/1999 | Saadat et al. | |
| 6,042,030 A | 3/2000 | Howe et al. | |
| 6,346,102 B1 | 2/2002 | Harrington et al. | |
| 6,705,323 B1 | 3/2004 | Nikolchev et al. | |
| 7,621,276 B2 * | 11/2009 | Tal et al. | 128/831 |
| 7,669,601 B2 * | 3/2010 | Tal | 128/831 |
| 8,181,653 B2 * | 5/2012 | Tal et al. | 128/831 |
| 2002/0198547 A1 | 12/2002 | Schultz | |
| 2003/0066533 A1 | 4/2003 | Loy | |
| 2004/0009205 A1 | 1/2004 | Sawhney | |
| 2005/0125022 A1 | 6/2005 | Ravikumar et al. | |
| 2005/0171569 A1 | 8/2005 | Girard et al. | |
| 2005/0192616 A1 | 9/2005 | Callister et al. | |
| 2008/0302368 A1 | 12/2008 | McGuckin, Jr. et al. | |

FOREIGN PATENT DOCUMENTS

| | | |
|---|---|---|
| EP | 0011143 | 5/1980 |
| EP | 0208653 | 1/1987 |
| FR | 2538243 | 6/1984 |
| IT | 1053357 | 8/1981 |
| JP | 59-0214444 | 2/1984 |
| JP | 61-42914 | 3/1986 |
| WO | WO90/01310 | 2/1990 |
| WO | WO2006/088909 | 6/2006 |

* cited by examiner

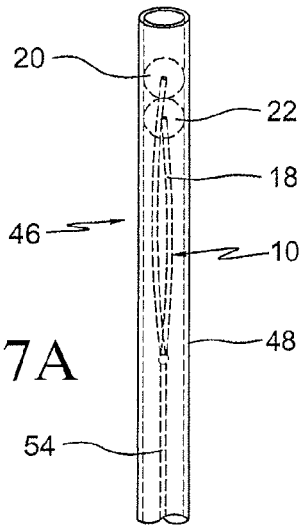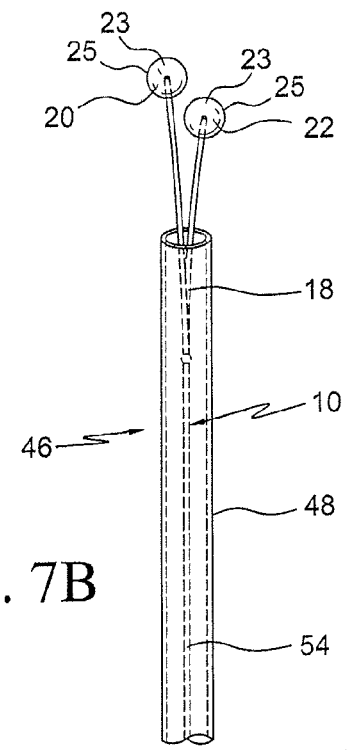
FIG. 7A    FIG. 7B
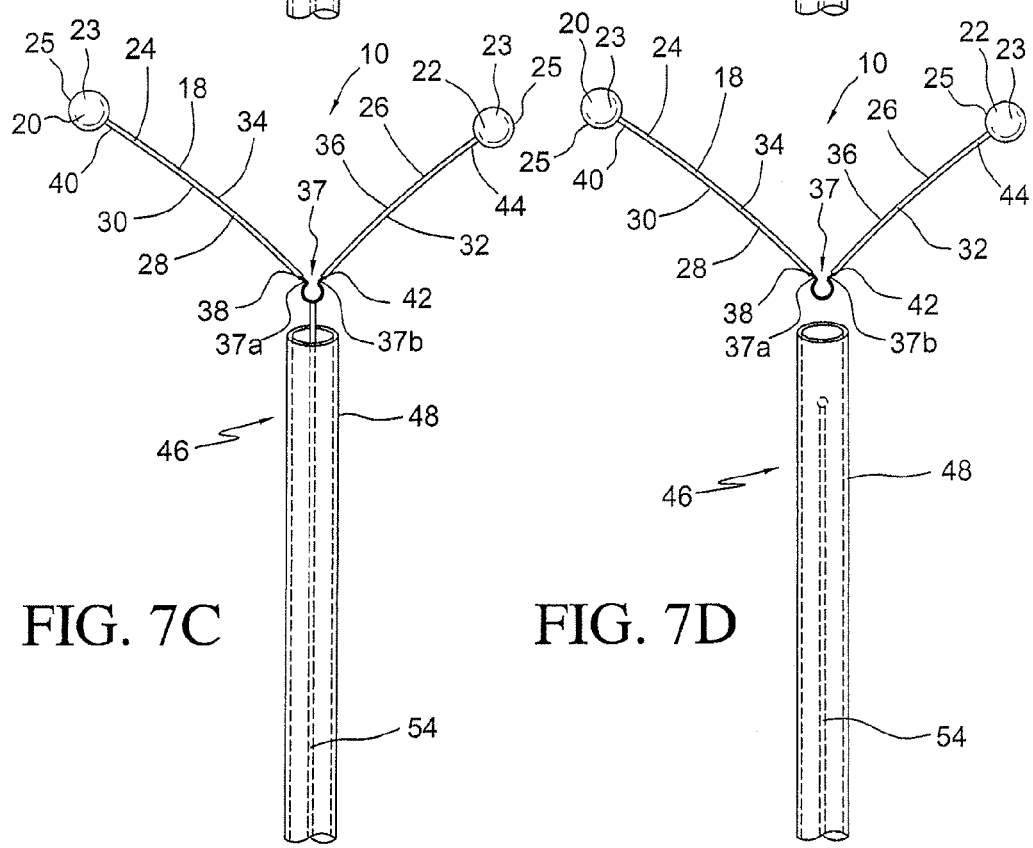
FIG. 7C    FIG. 7D

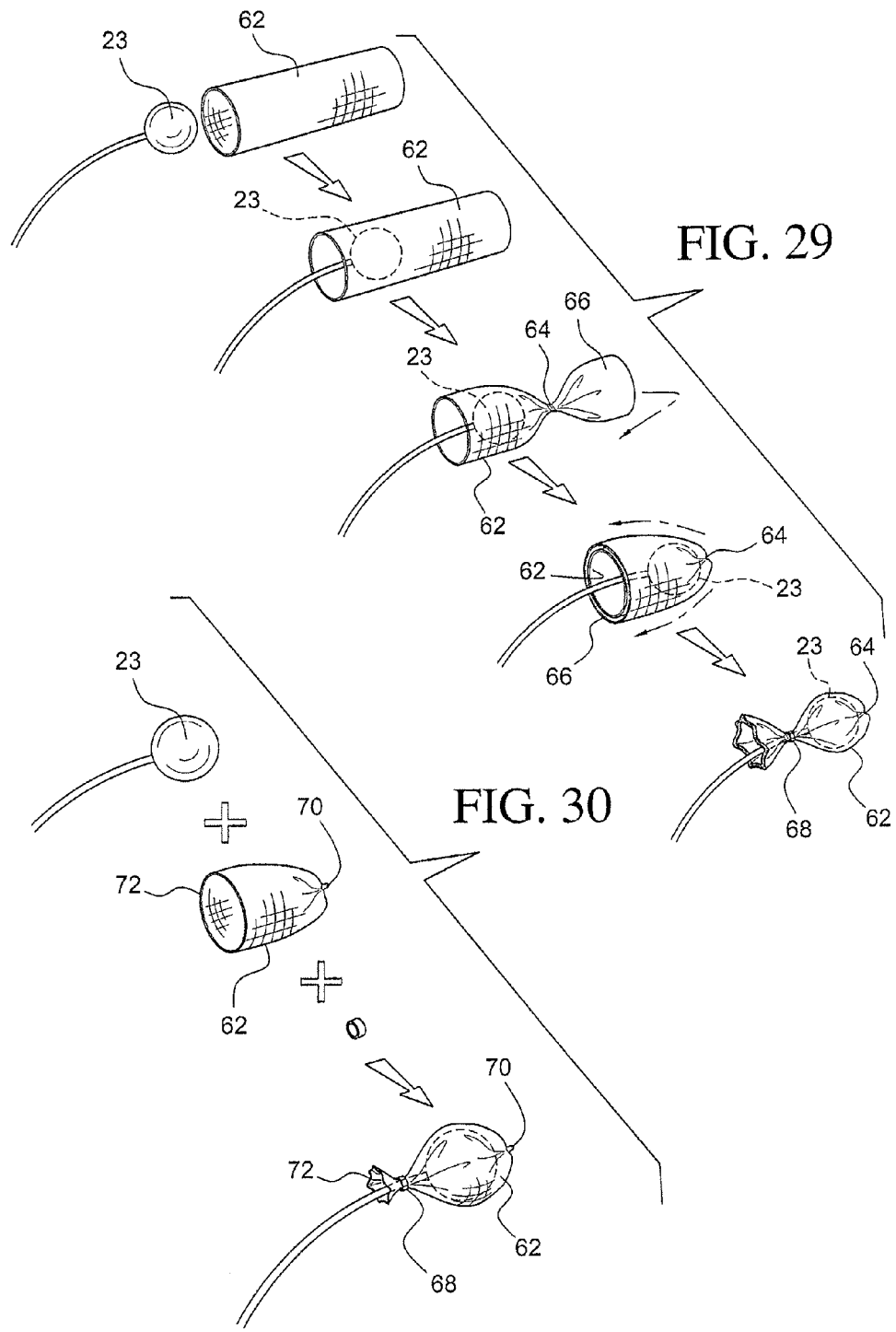

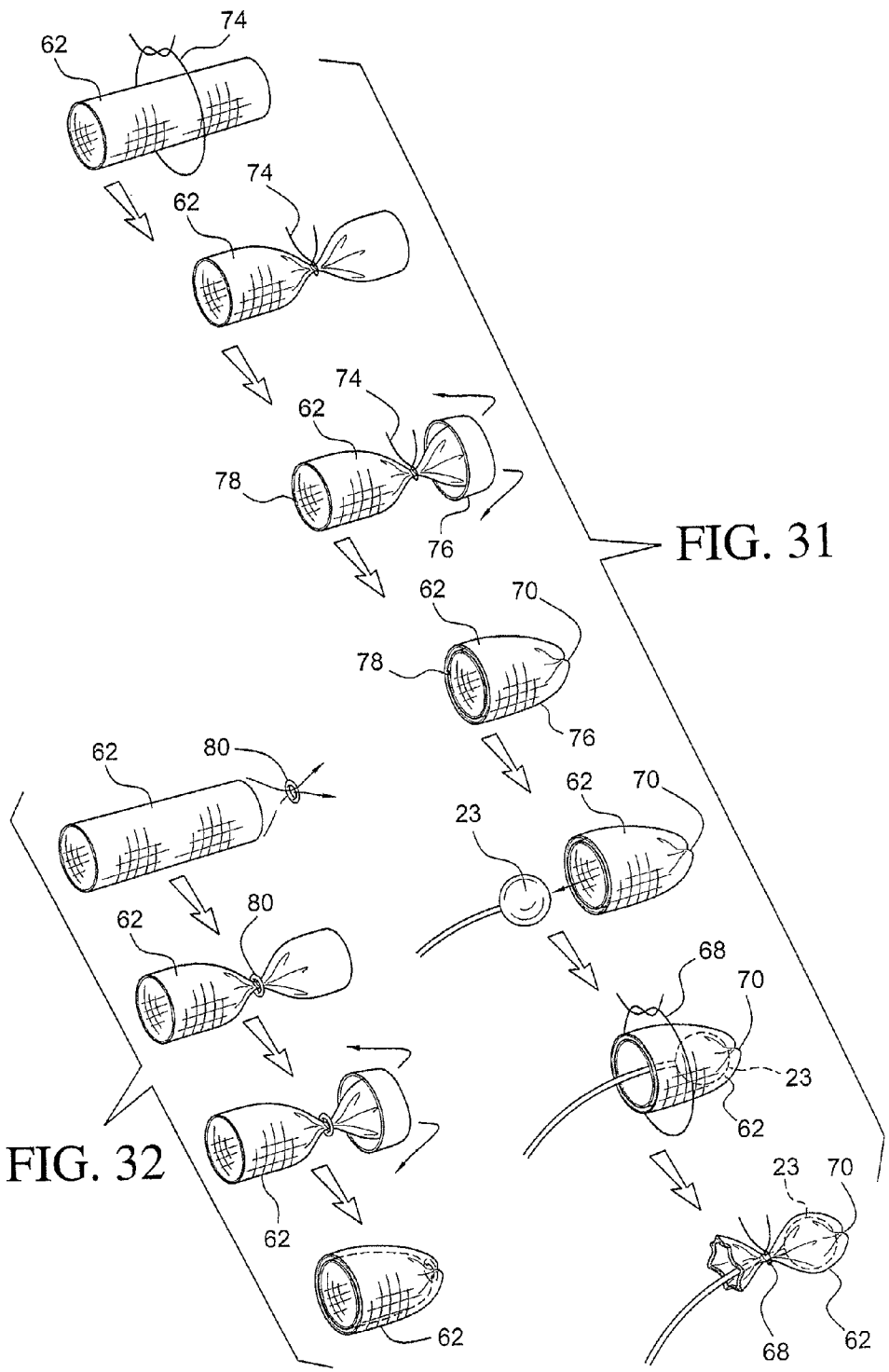

INTRAUTERINE DEVICE

CROSS REFERENCE TO RELATED APPLICATIONS

This application is a continuation-in-part of U.S. patent application Ser. No. 12/353,770, filed Jan. 14, 2009, entitled "INTRAUTERINE FALLOPIAN TUBE OCCLUSION DEVICE", which is now U.S. Pat. No. 8,181,653, the '770 application claims the benefit of U.S. Provisional Application Ser. No. 61/006,454, filed Jan. 15, 2008, entitled "INTRAUTERINE FALLOPIAN TUBE OCCLUSION DEVICE", and the '770 application is a continuation-in-part of U.S. patent application Ser. No. 11/892,560, filed Aug. 23, 2007, entitled "INTRAUTERINE FALLOPIAN TUBE. OCCLUSION DEVICE", which is now U.S. Pat. No. 7,621,276, which is a continuation-in-part of U.S. patent application Ser. No. 11/884,027, filed Aug. 9, 2007, entitled "INTRAUTERINE FALLOPIAN TUBE OCCLUSION DEVICE AND METHOD FOR USE", which is now U.S. Pat. No. 7,669,601, which is the National Stage of International Application No. PCT/US2006/005245, filed Feb. 15, 2006, entitled "INTRAUTERINE FALLOPIAN TUBE OCCLUSION DEVICE AND METHOD FOR USE", which claims the benefit of U.S. Provisional Patent Application Ser. No. 60/653,743, filed Feb. 15, 2005, entitled "INTRAUTERINE FALLOPIAN TUBE OCCLUSION DEVICE".

BACKGROUND OF THE INVENTION

1. Field of the Invention

The invention relates to an intrauterine device and method for use. More particularly, the invention relates to an intrauterine device that uses the unique shape of the uterine cavity to ensure delivery and proper positioning thereof. The intrauterine device employs plug members for bearing against the wall of the uterus in a manner preventing conception. The invention also relates to a delivery mechanism utilizing the device described herein to deliver medication and/or other therapeutic agents to the uterus and/or fallopian tube anatomy.

2. Description of the Related Art

Several types of intrauterine devices (IUDs) are available and used worldwide. There are inert IUDs, copper IUDs and hormone impregnated IUDs. There is ongoing controversy regarding the mechanisms of action of IUDs in humans. Classically, the view was that the IUD in humans acted predominantly after fertilization to prevent implantation, but evidence has accumulated for some effects before fertilization. As a general rule, the pre-fertilization effects are not enough to prevent fertilization and, therefore, the post-fertilization effects are most important. The post-fertilization mechanisms of action of the IUD include slowing or speeding the transport of the early embryo through the fallopian tube, damage to or destruction of the early embryo before it reaches the uterus, and prevention of implantation. This mechanism of action is perceived as an early abortion by some, and prevents many patients from using IUDs as a temporary mode of contraception. Another problem with IUDs is expulsion from the uterus and subsequent unwanted pregnancy. Other potential complications of IUDs are uterine infection, uterine perforation and most important ectopic pregnancy. Ectopic pregnancy is a condition where the embryo has implanted outside of the uterine cavity, usually in the fallopian tube. This condition is also hazardous to the patient and can lead to internal bleeding and severe morbidity and even mortality. This potential complication also deters patients from the use of IUDs.

With the foregoing in mind, a need exists for an improved intrauterine system replacing currently marketed IUDs and other methods of contraception, such as, tubal ligation.

SUMMARY OF THE INVENTION

It is, therefore, an object of the present invention to provide an intrauterine device for applying pressure to the walls of the uterine cavity including a resilient body having an elongated member which includes a first end and a second end which are resiliently biased away from each other. The first end of the elongated member includes a first leg having a first end and a second end. The second end of the elongated member includes a second leg having a first end and a second end. A connection member is positioned between the first end of the first leg and the first end of the second leg. A first plug member is secured at the second end of the first leg and a second plug member is secured at the first end of the second leg. The first and second plug members are shaped and dimensioned for bearing against the walls of the uterine cavity as the elongated member spreads outwardly with the first end and the second end moving apart.

It is also an object of the present invention to provide a method for preventing conception within the uterine cavity including the step of delivering an intrauterine device into the uterine cavity. The intrauterine device includes an elongated member with a first end and second end. A first plug member is secured at the first end of the elongated member and a second plug member is secured at the second end of the elongated member. The method further includes causing the intrauterine device to apply pressure within the uterine cavity in a manner that will alter the shape of the uterine cavity over time thus preventing conception.

It is another object of the present invention to provide a method for delivering an intrauterine device including the steps of advancing the intrauterine device into the uterine cavity. The intrauterine device includes an elongated member with a first end and second end, and a first plug member secured at the first end of the elongated member and a second plug member secured at the second end of the elongated member. The method further includes releasing the intrauterine device. Release results in (a) the first and second plug members first moving outwardly due to stored outward bias in the elongated member, (b) the first and second plug members then moving upwardly within the uterine cavity, (c) the first and second plug members then moving into contact with respective opposed walls of the uterine cavity and (d) the first and second plug members applying pressure to respective opposed walls of the uterine cavity to prevent conception within the uterine cavity.

It is a further object of the present invention to provide a method for preventing conception within the uterine cavity including the step of delivering an intrauterine device into the uterine cavity for positioning between lateral walls of the uterine cavity. The intrauterine device includes an elongated member with a first end and second end, and a first plug member secured at the first end of the elongated member and a second plug member secured at the second end of the elongated member. The method also includes the step of causing the intrauterine device to expand within the uterine cavity such that a distance between the first plug member and the second plug member is greater than the distance between opposed lateral walls of the uterine cavity.

Other objects and advantages of the present invention will become apparent from the following detailed description

BRIEF DESCRIPTION OF THE DRAWINGS

FIGS. 7A to 7D are detailed views showing the delivery apparatus for use in accordance with a preferred embodiment of the present invention with the steps of forcing the intrauterine device from within a container via a delivery rod.

FIGS. 8 to 13 are various views showing retrieval of the intrauterine device shown with reference to FIG. 1, while

FIGS. 29, 30, 31 and 32 show the steps associated with various techniques for the application of a tissue in-growth member to the plug member.

DESCRIPTION OF THE PREFERRED EMBODIMENTS

Figure 1:
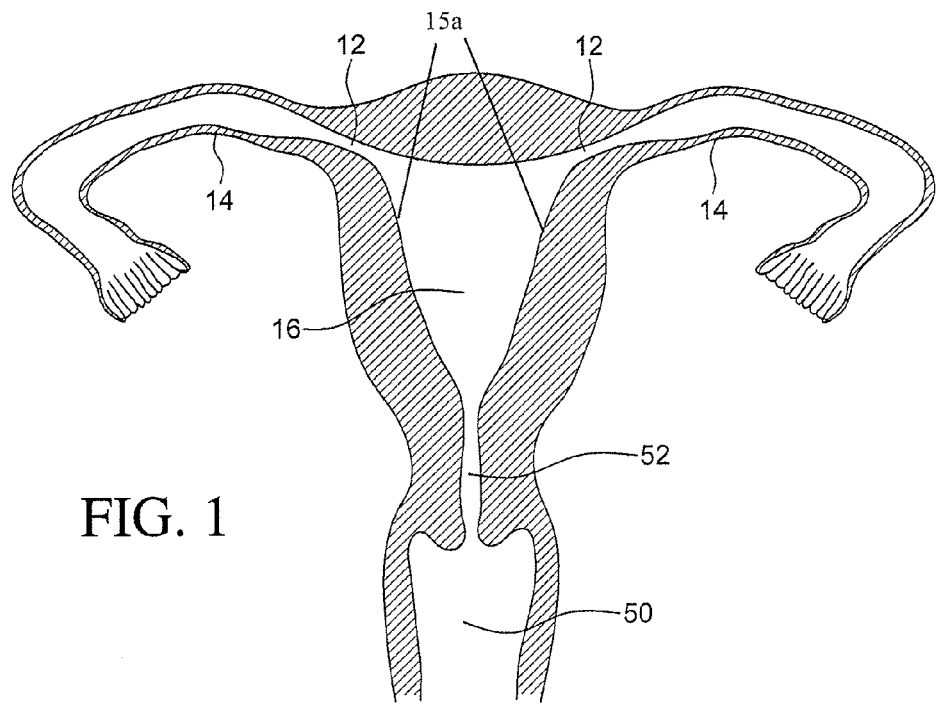
FIGS. 1 to 6 are various views showing delivery of the intrauterine device in accordance with a preferred embodiment of the present invention.
Figure 2:
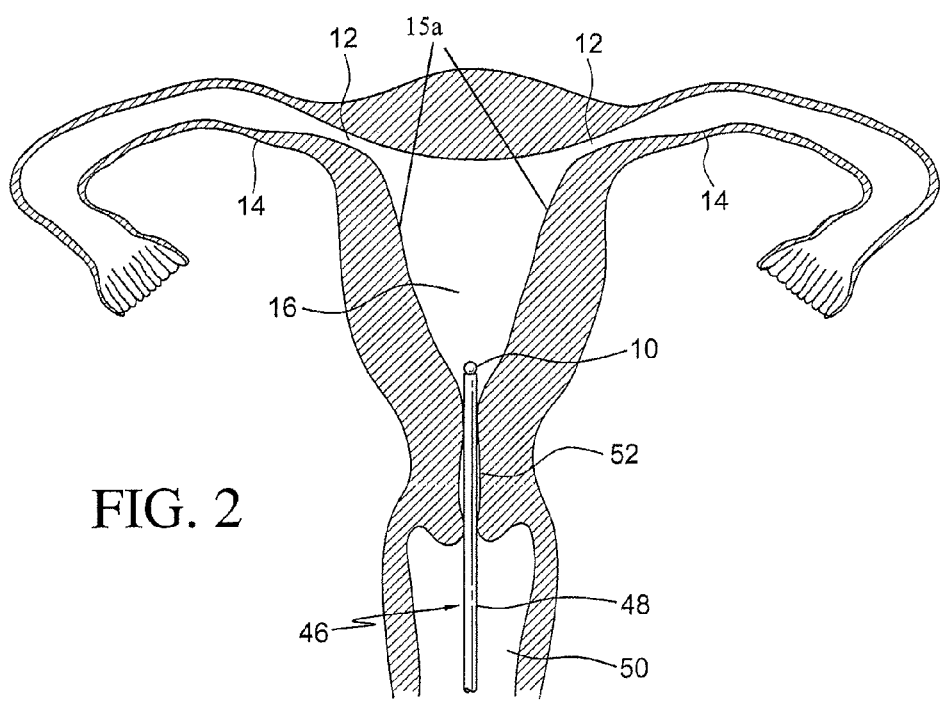
Figure 3:
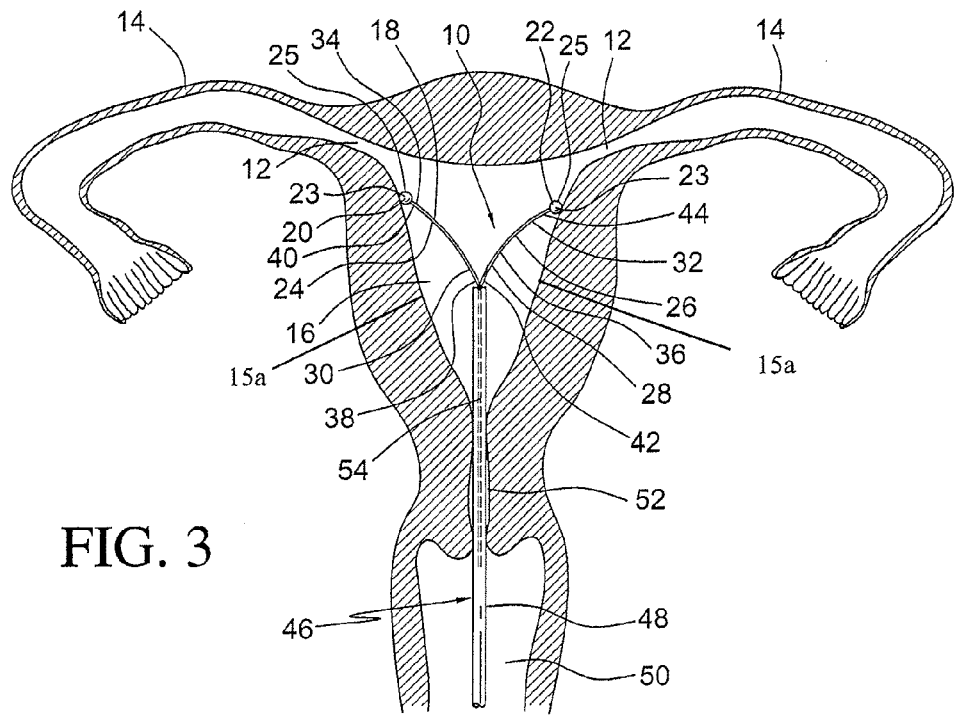
Figure 4:
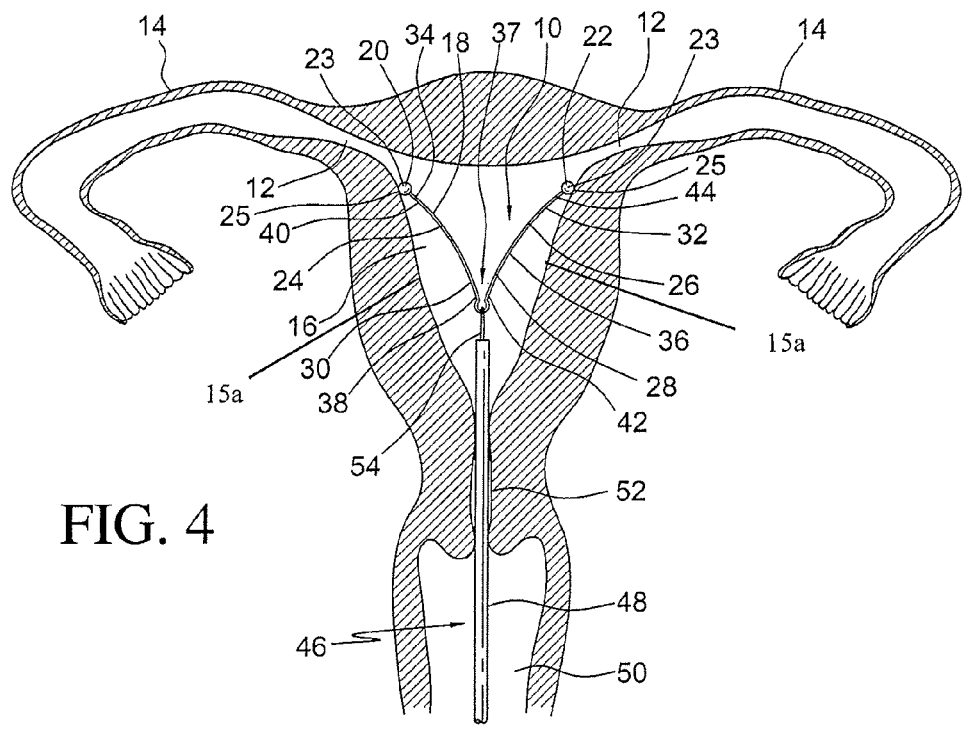
Figure 5:
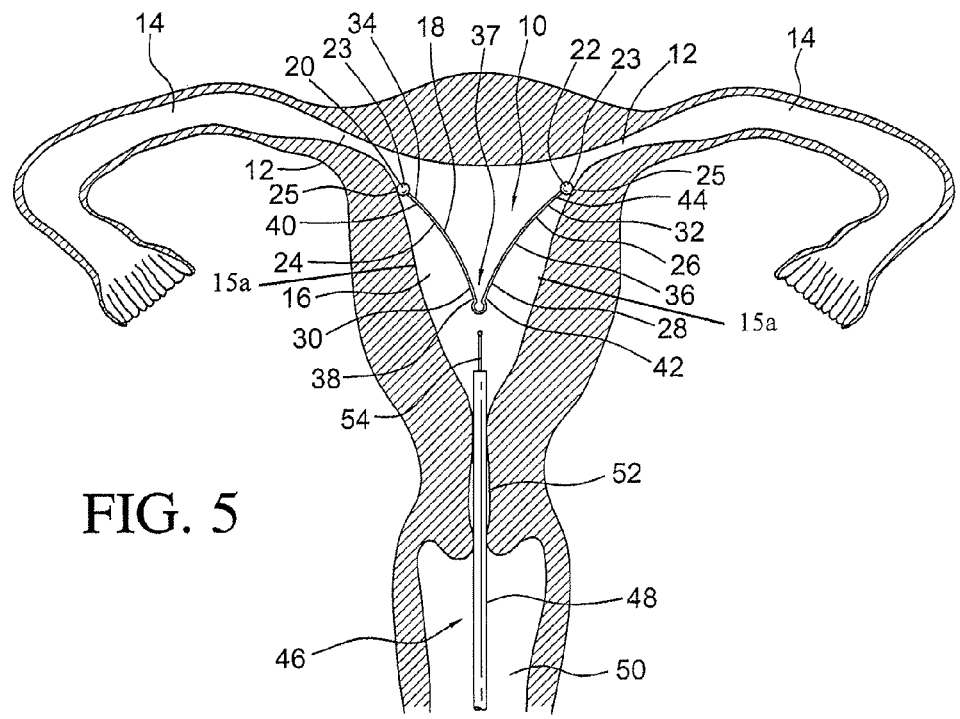

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention. Since various embodiments are disclosed herein, similar reference numerals have been employed throughout the present disclosure when referring to similar elements in the various embodiments and where such use of similar references numerals is deemed appropriate.

With reference to the various figures, an intrauterine device 10 in accordance with a preferred embodiment of the present invention is disclosed that will actively bear against the lateral walls 15a of the uterine cavity 16 using the shape of the uterine cavity 16 as a guide to the proper positioning of the intrauterine device 10. The present intrauterine device 10 allows safe contraception without the use of hormones. As will be appreciated based upon the following disclosure, the present intrauterine device 10 is flexible and, in accordance with a preferred embodiment, is made from a Nitinol resilient body 18 and two 3 mm POREX, a porous polyethylene manufactured by Porex Technologies, plug members 20, 22. The use of Nitinol in the construction of the resilient body 18 facilitates gentle and constant pressure on the lateral uterine walls 15a. The Nitinol offers a unique property of constant lateral pressure in various uterine sizes. Because of this reason, the present intrauterine device 10 is "one size fits all". Constant gentle lateral pressure along the lateral walls 15a of the uterine cavity 16 prevents expulsion as the intrauterine device 10 is always situated in the upper part of the uterine cavity 16. When properly positioned, the plug members 20, 22 are within centimeters of the respective orifices 12 of the fallopian tubes 14, at a position beneath the orifices 12 and along the lateral walls 15a of the uterine cavity 16; preferably at a position within 1 cm inferior to the orifices 12 of the fallopian tubes 14. The plug members 20, 22 are consistently situated in the vicinity of the fallopian tube orifices 12. The plug members 20, 22 offer a larger contact point with the lateral walls 15a of uterine cavity 16 making perforation and discomfort unlikely. This was proven in the clinical setting. The intrauterine device 10 sits in the uterus and exerts some lateral pressure which slightly distorts the uterine cavity 16. In accordance with a preferred embodiment, the pressure applied is at least approximately 0.01 ft·lb, more preferably between approximately 0.01 ft·lb and approximately 0.025 ft·lb. This gentle distortion likely disturbs uterine contraction and possibly further assists the intrauterine device 10 in preventing intrauterine pregnancy. This combined action of foreign body and gentle pressure of the lateral walls 15a of the uterus likely explains the excellent clinical results with the present intrauterine device 10. The gentle constant lateral pressure with the present intrauterine device 10 makes the device completely pain free to women and offers the advantage of pain free insertion and placement compared to other stiffer IUDs.

Figure 45:
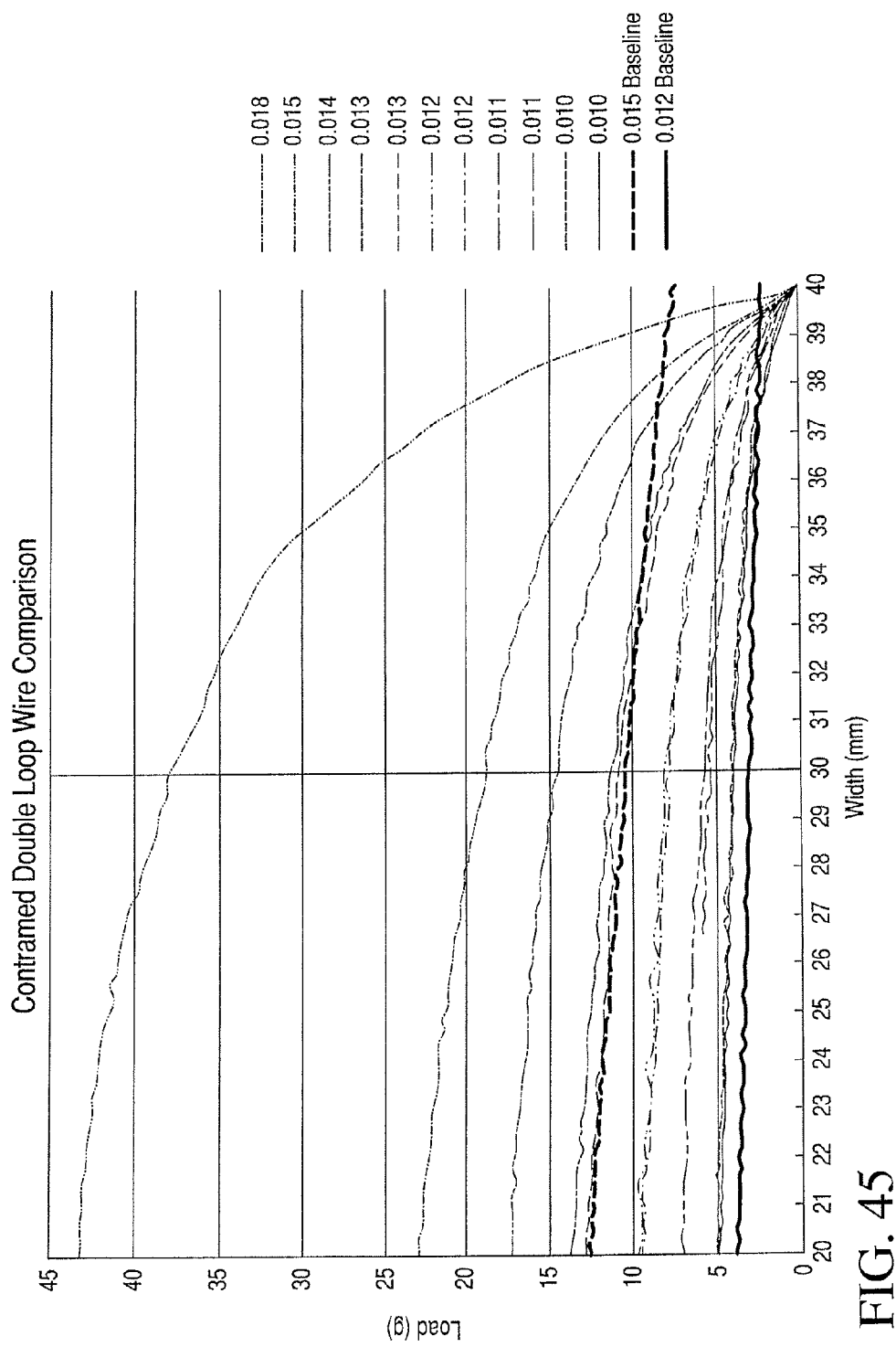
FIG. 45 is a graph showing load profiles for the resilient body in accordance with the present invention.

With the foregoing in mind, and as will be discussed below with regard to tissue in-growth, control of the applied force is important because the applied force, or pressure, causes distortion of the lateral walls 15a of the uterine cavity 16. With this in mind, the deployed intrauterine device 10 is designed to apply sufficient pressure to slightly distort the uterine cavity 16 preventing conception. More particularly, testing has revealed the plug members must preferably span a distance of approximately 18 mm to approximately 54 mm depending upon the anatomical characteristics of the patient. The elongated member (regardless of the embodiment as described herein) is, therefore, capable of moving (for example, spreading based upon the inherent spring bias) to spread the first and second plug members from between approximately 18 mm and 54 mm apart. The present intrauterine device, in particular, the elongated member, must further be capable of applying a relatively consistent force (for example, a load of at least approximately 0.01 ft·lb in accordance with a preferred embodiment) while the plug members are positioned within the desired span between the lateral walls 15a of the uterine cavity 16. In accordance with a preferred embodiment, the load is approximately 0.01 ft·lb to approximately 0.025 ft·lb. Each of the embodiments disclosed herein attempts to accommodate these requirements with the controlled application of force. For example, the embodiment described with reference to FIGS. 1 to 6 is preferably manufactured from Nitinol which has been found capable of providing relatively consistent application of force across a wide range of plug member spans (see FIG. 45 showing the load profiles for Nitinol at various rod thicknesses). Irritation (and/or damage) encouraging tissue in-growth may be further facilitated by applying corrosive material to the surface of the plug member.

With the foregoing in mind, the distance between the first and second plug members 20, 22 when the intrauterine device 10 is fully extended must be greater than the distance between the lateral walls 15a of the uterine cavity adjacent the fallopian tube orifices 12 when the uterine cavity is in its relaxed state. It should be appreciated that it has been determined the average intra-ostial distance in nulliparous women is 29.2 mm and the average intra-ostial distance in parous women is 30.0 mm. "Assessment Of The Uterine Cavity And The Intraostial Distance Using Hysterosalpingography", *Fertility and Sterility*, Volume 88, Supplement 1, September 2007, Page S202, J. G. Bromer, F. Sanguinetti, M. Tal, P. Patrizio. Obstetrics, Gynecology, and Reproductive Sciences, Yale University School of Medicine, New Haven, Conn.; Department of Radiology, Yale University School of Medicine, New Haven, Conn.

As will be appreciated based upon the following disclosure, the present invention provides a delivery system that is simple to use and intuitive. The size of the delivery system is very small and allows insertion without pre dilatation, pain or use of local anesthesia. Insertion by the gynecologist is blinded and placement is consistently reliable. The present intrauterine device 10 is very well seen on transvaginal ultrasound. The plug member 20, 22 are well visualized and echogenic. The location of the plug members 20, 22 in the lateral part of the uterus is consistently seen on ultrasound. It is contemplated the present intrauterine device 10 can have copper on it. In this case, the copper can be placed in the vicinity of the plug members 20, 22 and be delivered in the vicinity of the fallopian tubes 14, making the likelihood of ectopic pregnancy even less likely.

The shape of the uterine cavity 16 is illustrated in FIG. 1. The uterine cavity 16 is normally in continuation with the fallopian tubes 14. For fertilization, the sperm migrates from the uterine cavity 16 into the fallopian tube 14. The force applied by the intrauterine device 10 in bearing against the lateral walls 15a of the uterine cavity 16 prevents fertilization. For successful pregnancy, a normal uterine environment is needed as well as normal uterine contractions. The pressure on the lateral walls 15a of the uterine cavity 16 distorts normal uterine contractions and further reduces the likelihood of pregnancy, thus improving the effectiveness of the present intrauterine device 10.

The present invention provides an intrauterine device 10 that is either permanent, removably permanent or temporary, in part or wholly, utilizing the unique shape of the uterine cavity 16. The present invention also allows nonsurgical contraception that can be done as an office procedure and without the need for surgery or the necessity for visualization either radiologically, ultrasonically, or with a hysteroscope. The present intrauterine device 10 uses radial force and inherent properties in its construction to prevent migration or expulsion of the intrauterine device 10. As such, the present invention may be used with the following procedures: contraception, either permanent or temporary; and potential treatment of other causes of abnormal uterine bleeding or pelvic pain. The present intrauterine device 10 may be adaptable to other therapies or treatments, such as localized medicinal delivery, with only an alteration to the barrier system.

As briefly discussed above, the present invention provides a method and apparatus for preventing conception wherein two plug members 20, 22 bear against the lateral walls 15a of the uterine cavity 16 by spreading them as far apart as the anatomy of the uterus permits and allowing the pressure generated as a result of spreading to be applied to the lateral walls 15a of the uterine cavity 16. For example, and as will be appreciated based upon the following disclosures, various structures may be employed in creating the necessary pressure. In accordance with various preferred embodiments described herein, the length between the plug members 20, 22 is adjusted by flexion of the elongated member 18 of the intrauterine device 10. As will be appreciated by the following disclosures, it is not necessary that the intrauterine device 10 rely upon spring-like or resilient structures to achieve the creation of pressure but may employ other mechanical features as described herein.

In accordance with a preferred embodiment, the unique shape of the uterine cavity 16 allows the present intrauterine device 10 to be inserted without (or with) visualization into the uterine cavity 16 for positioning in a manner that bears against the lateral walls 15a of the uterine cavity 16. The unique shape also maintains the intrauterine device 10 in place without the need for sutures or any other anchoring mechanism. The present intrauterine device 10 is also readily removable. The presence of the intrauterine device 10 in the uterine cavity 16 acts as an IUD by preventing fertilization and thereby averts the destruction of an embryo, which is considered the major mechanism of an IUD's birth control efficacy. This makes the present intrauterine device 10 more acceptable to some patients and allows its use in a larger part of the population.

As mentioned above, the present intrauterine device 10 functions primarily as an IUD. The present invention also relates to a method and apparatus for transvaginal implantation and removal of the intrauterine device 10.

As discussed below in greater detail, the present intrauterine device 10 is composed of a resilient body 18 with first and second plug members 20, 22 at the respective first and second ends 24, 26 of the resilient body 18. The resilient body 18 is preferably made from a shape memory alloy metal (such as, Nitinol) or any other material (or combination of materials) that will create an appropriate load providing an appropriate lateral force as the intrauterine device 10 is deployed within the uterine cavity 16. The outwardly directed lateral force generated by the resilient body 18 brings the first and second plug members 20, 22 into contact with the lateral walls 15a of the uterine cavity 16 creating opposed force along the lateral walls 15a of the uterine cavity 16 and causing the intrauterine device 10 to ride up the lateral walls 15a of the uterine cavity 16 until the first and second plug members 20, 22 seat along the lateral walls 15a of the uterine cavity 16 bearing against the walls 15a thereof at a position adjacent the orifices 12 of the fallopian tubes 14; preferably at a position within 1 cm inferior to the orifices 12 of the fallopian tubes 14. It should also be noted the plug members of the intrauterine device 10 might simply be initially applied at the location where pressure is to be applied and not ride up the lateral walls. It has further been found the plug members 20, 22 move laterally indenting the contour of the uterine cavity 16 after placement. It is also contemplated the resilient body could be made out of resorbable magnesium alloy wire or resorbable plastic.

Although Porex porous polyethylene is disclosed above as a preferred material for use in the construction of the plug members 20, 22, the plug members 20, 22 can be made from various materials such as metals, plastics, elastomers such as silicone, or combinations thereof, and be impregnated with various medications and compounds. As will be appreciated based upon the following disclosure, it is further contemplated the material composition of the plug members 20, 22 could be selected such that it would encourage tissue in-growth or prevent (or minimize) tissue in-growth, therefore controlling the ease of removal of the intrauterine device 10 after the passage of time. When tissue in-growth is desired, molded materials such as specially processed porous silicone, polyethylene, polypropylene, etc. could be used in the manufacture of the plug members 20, 22 to allow tissue in-growth. In addition to generally molded constructions, the plug members 20, 22 may take the form of a mesh or coil with or without a tissue in-growth member (for example, of a mesh material) for anchoring to surrounding tissue. The resilient body 18 and/or plug members 20, 22 can be either inert, meaning without any medication or substance on them, or released from them, or they can be impregnated or coated, in part or wholly, with any medication such as hormones or metal, such as, copper. The plug members 20, 22 can also be covered with any other kind of spermicide or other materials. As a result, the present intrauterine device 10 may be used as a medication delivery device, supplying medication to specific locations and then retrieved in part or wholly as discussed below with reference to FIGS. 8-13.

The intrauterine device 10 utilizes the shape of the uterine cavity 16 and conforms the shape of the first and second plug members 20, 22 to the lateral walls 15a of the uterine cavity 16, and/or the plug members 20, 22 elastically or deformably conform to the lateral walls 15a of the uterine cavity 16. As briefly mentioned above, the plug members 20, 22 can contain any kind of material or medicine to be delivered to the lateral walls 15a of the uterine cavity 16. Once the material or medicine is delivered, the intrauterine device 10 can be removed in the manner discussed below with reference to FIGS. 8 to 13.

Referring to the various figures, and in accordance with a preferred embodiment of the present invention, the present intrauterine device 10 includes a resilient body 18 exhibiting spring-like characteristics. The resilient body 18 has first and second plug members 20, 22 secured at opposite ends thereof. In accordance with a preferred embodiment of the present invention, the first and second plug members 20, 22 are shaped and dimensioned to ride up the lateral walls 15a of the uterine cavity 16 until they seat along the lateral walls 15a of the uterine cavity 16 at a position adjacent the orifices 12 of the fallopian tubes 14 as the resilient body 18 spreads outwardly with the first end 24 and second end 26 thereof moving apart and bearing upon the lateral walls 15a of the uterine cavity 16 in a manner preventing conception. Optimal bearing pressure has been found to be achieved when the plug members 20, 22 have a diameter from approximately 1 mm to 8 mm, more preferably 3 mm. This optimal plug member also allows delivery through a small delivery system that is convenient and pain free to the patients. This size of plug member also minimized the risk of uterine perforation, a well known risk of currently available intrauterine devices.

More particularly, the resilient body 18 includes an elongated member 28 having a first end 30 and a second end 32. The first end 30 of the elongated member 28 is composed of a first leg 34 and the second end 32 of the elongated member 28 is composed of a second leg 36. The first plug member 20 is secured at the distal end of the first end 30 of the elongated member 28 and the second plug member 22 is secured at a distal end of the second end 32 of the elongated member 28.

The first leg 34 includes a first end 38 and second end 40, and the second leg 36 includes a first end 42 and second end 44. The first ends 38, 42 of the respective first and second legs 34, 36 are respectively connected, while the second ends 40, 44 of the first and second legs 34, 36 are respectively free and are provided with, and coupled to, the respective first and second plug members 20, 22. A connection member 37 resiliently (or rigidly) couples the first ends 38, 42 of the first and second legs 34, 36 in a manner biasing the second ends 40, 44 of the first and second legs 34, 36 from each other when they are not restrained in a manner discussed below in greater detail.

With this in mind, the first leg 34 and the second leg 36 are angularly oriented relative to each other creating an elongated member 28 which is substantially V-shaped when the first leg 34 and the second leg 36 are allowed to move away from each other based upon the outward bias inherent in the connection member 37 between the first and second legs 34, 36. The inherent bias in the connection member 37 is created through the utilization of spring materials or shape memory materials in the construction of the resilient body 18, in particular, the connection member 37. With this in mind, the connection member 37 includes a substantially circular configuration with a first end 37a connected to the first end 38 of the first leg 34 and a second end 37b connected to the first end 42 of the second leg 36 (see FIGS. 7C and 7D). The connection member 37 is formed with an inherent outward bias that forces the first leg 34 and the second leg 36 outwardly upon deployment.

In addition, and in accordance with a preferred embodiment, the first leg 34 and the second leg 36 are formed with an outward bow when fully extended. This outward bow can store further outward bias when the intrauterine device 10 is compressed for storage and deployment. In accordance with a preferred embodiment, when the intrauterine device 10 is entirely unrestrained the first and second legs 34, 36 will form a maximum open angle of approximately 150 degrees or other appropriate angular dimension so as to adequately contribute to the aforementioned outward bias. This angle forms a geometry preventing the first and second legs 34, 36 from moving away from a fundamentally centralized location in the uterine cavity 16 (see FIGS. 1 to 6). That is, the shape of the resilient body 18, a sort of triangle, only spreads so wide so that it would bump into the lateral walls 15a of the uterine cavity 16, that way staying located in the center of the uterine cavity 16.

The combination of the outwardly bowed first and second legs 34, 36 and the connection member 37 allows for the creation of an outwardly directed load providing an appropriate lateral force to bring the first and second plug members 20, 22 into contact with the lateral walls 15a of the uterine cavity 16 causing the intrauterine device 10 to ride up the lateral walls 15a of the uterine cavity 16 until the first and second plug members 20, 22 seat along the lateral walls 15a of the uterine cavity 16 at a position adjacent the orifices 12 of the fallopian tubes 14 biasing the lateral walls 15a of the uterine cavity 16 outwardly in a manner preventing conception. As such, and as discussed herein in greater detail, the present intrauterine device 10 may be delivered by release within the uterine cavity 16 with automatic expansion resulting in controlled, self-positioning of the respective plug members 20, 22 along the lateral walls 15a of the uterine cavity 16.

Figure 14:
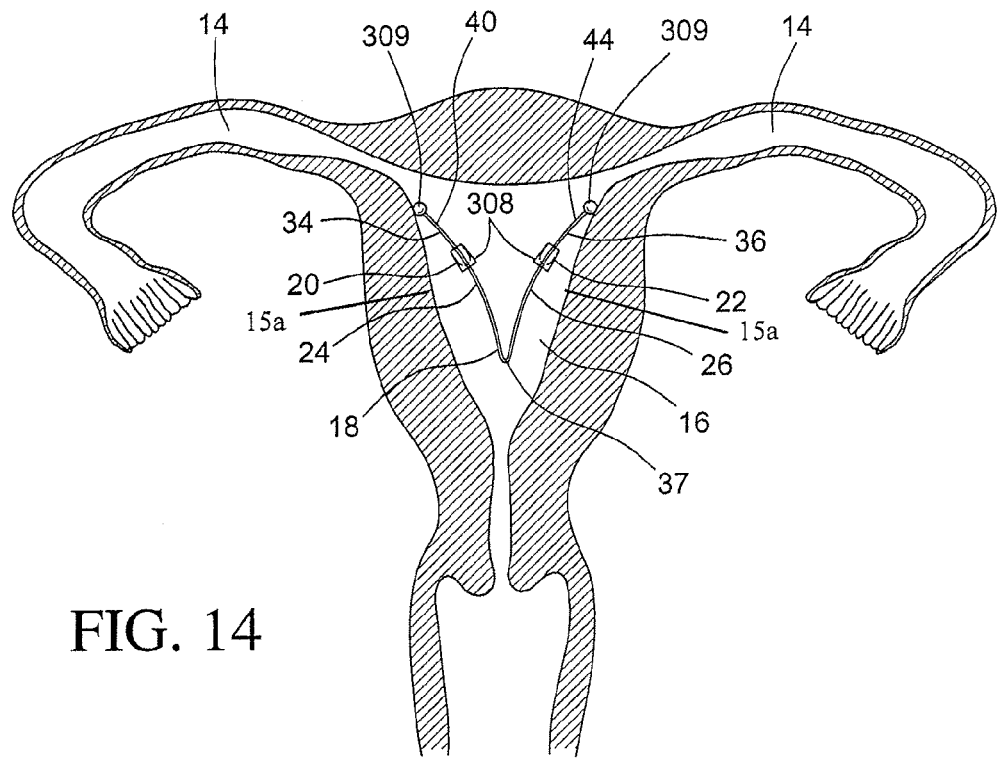
FIGS. 14 and 15 are schematics showing an alternate embodiment of the intrauterine device wherein the plug members ride on the first and second legs for sliding movement of the plug members relative to the respective first and second legs.
Figure 15:
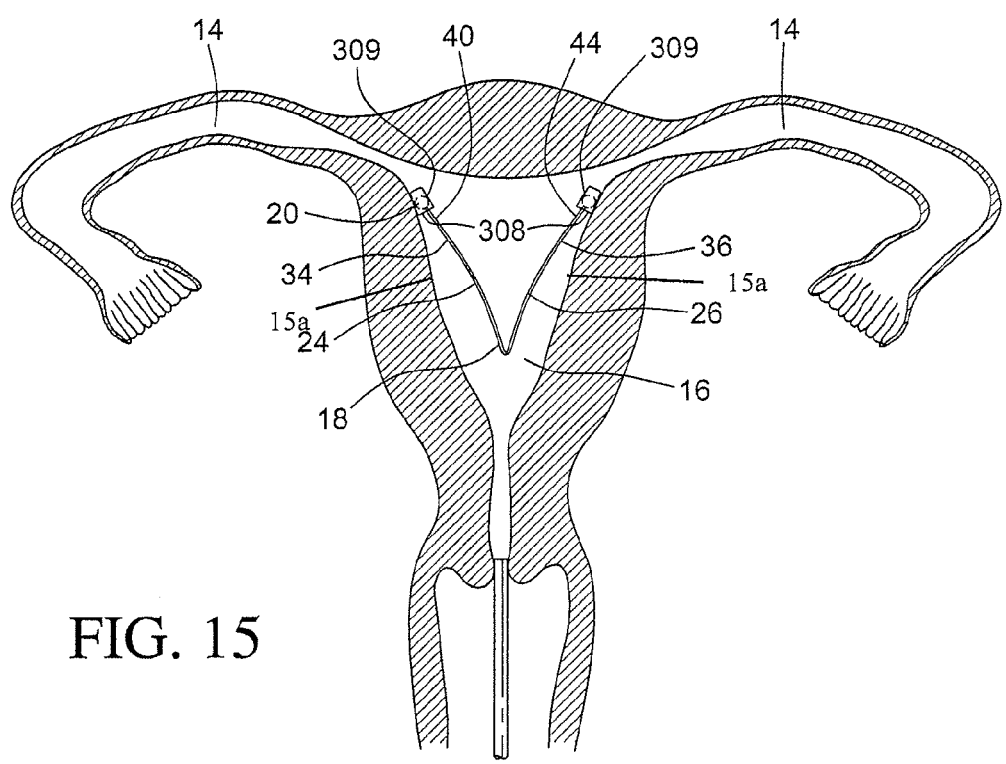

Referring to FIGS. 14 and 15, an alternate embodiment in accordance with the present invention is disclosed. In accordance with this embodiment, the plug members 20, 22 are designed to slide along the resilient body 18. In particular, the resilient body 18 is once again made from a shape memory alloy metal, or other appropriate resilient material, and is formed in the shape of a V such that the first and second ends 24, 26 of the resilient body 18 are directed toward the lateral walls 15a of the uterine cavity 16 when properly inserted within the uterine cavity 16. However, upon insertion, the plug members 20, 22 are located at a first position adjacent the connection member 37 linking the first and second legs 34, 36 (see FIG. 14). Once the resilient body 18 is positioned within the uterine cavity 16 with the second ends 40, 44 of the respective first and second legs 34, 36, that is, the first and second ends 24, 26 of the resilient body 18, positioned and seated along the lateral walls 15a of the uterine cavity 16 applying outward pressure thereto, the plug members 20, 22 are respectively moved upwardly along the first and second legs 34, 36 to a second position adjacent the second ends 40, 44 of the respective first and second legs 34, 36 where the plug members 20, 22 are positioned along the lateral walls 15a of the uterine cavity 16. With this in mind, each of the first and second plug members 20, 22 is formed with a central bearing aperture 308 through which the resilient body 18 passes during usage. Retention of the plug members 20, 22 at the second ends 40, 44 of the first and second legs 34, 36 is achieved by frictional retention due to the interaction between the central bearing apertures 308 and enlarged, spherical member 309 formed at the second ends 40, 44 of the respective first and second legs 34, 36.

Figure 16A:
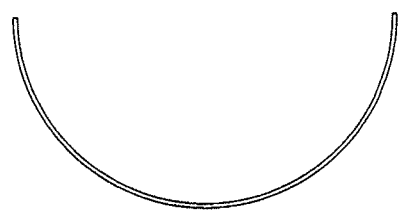
FIGS. 16A, 16B, 16C and 16D show various shapes of an elongated member that may be used in accordance with the present invention.
Figure 16B:
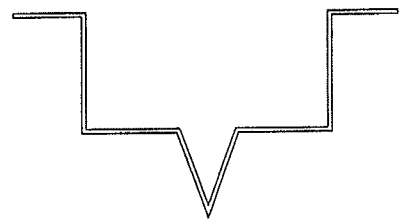
Figure 16C:
Figure 16D:
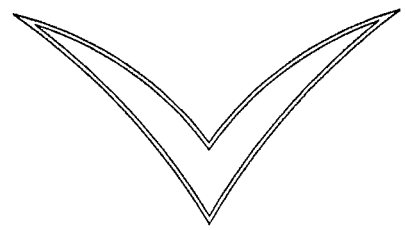

Although a preferred embodiment of the present invention employs a V-shaped elongated member with an outward bow as disclosed above, it is contemplated the elongated member 28 may be formed with a variety of shapes (whether in a fundamentally two dimensional planar configuration or a three dimensional planar configuration) so long as it retains its spring-like properties. Examples of contemplated shapes are shown in FIGS. 16A to 16D: FIG. 16A shows a U-shaped elongated member; FIG. 16B shows a stepped elongated member; FIG. 16C shows a crescent-shaped elongated member; and FIG. 16D shows a chevron-shaped elongated member.

Figure 17:
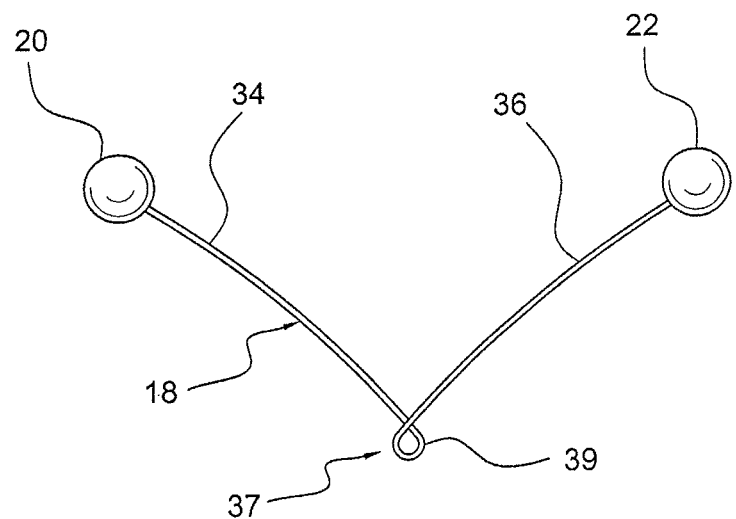
FIGS. 17, 18 and 19 show alternate embodiments of a connection member in accordance with the present invention.
Figure 18:
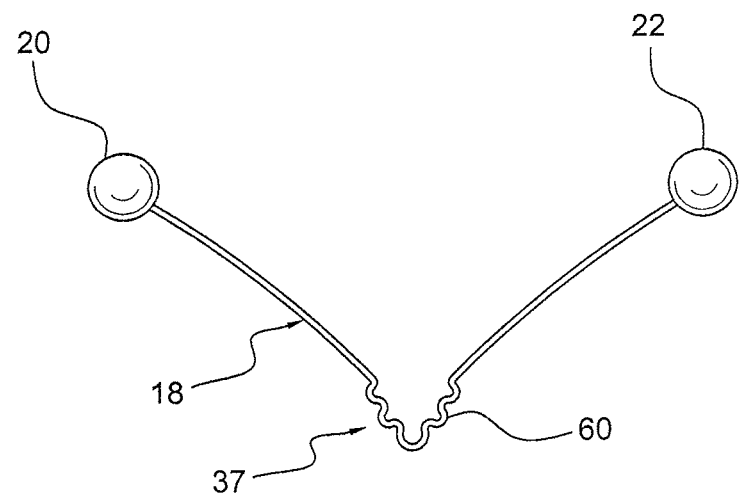

In addition, the spring bias may be imparted to the first leg 34 and the second leg 36 by constructing the connection member 37 with a spring biased loop 39 as shown in FIG. 17 or the spring bias may be controlled by incorporating bends 60 in the connection member 37 as shown in FIG. 18.

Figure 19:
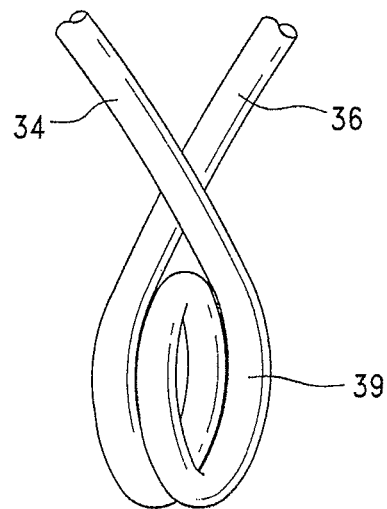
Figure 20A:
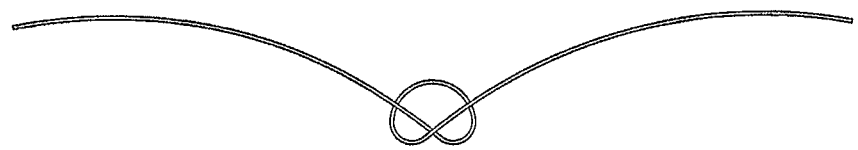
FIGS. 20A-K show other connection member structures in accordance with the present invention.
Figure 20B:
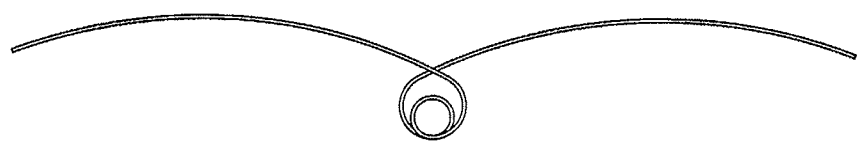
Figure 20C:
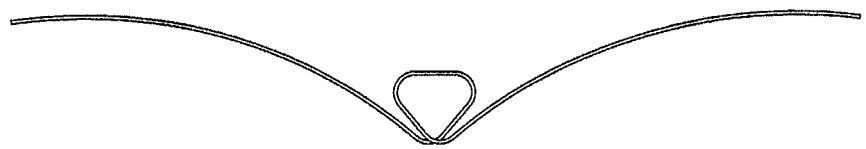
Figure 20D:
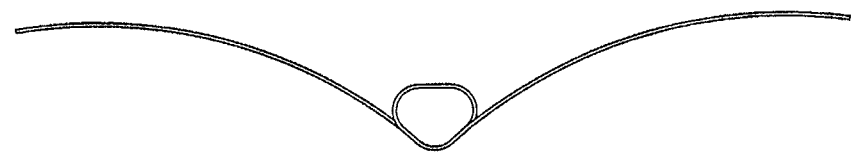
Figure 20E:
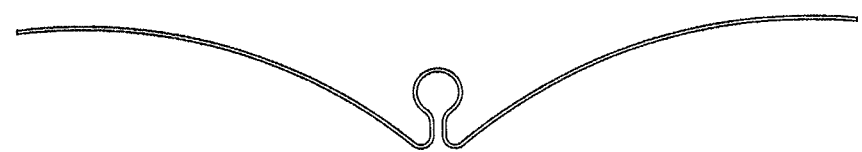
Figure 20F:
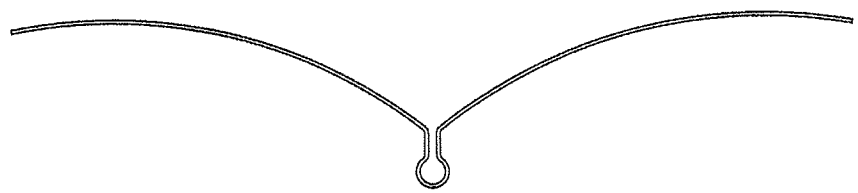
Figure 20G:
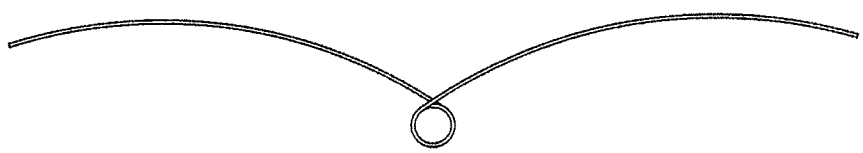
Figure 20H:
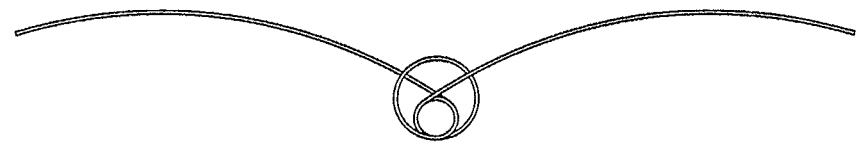
Figure 20I:
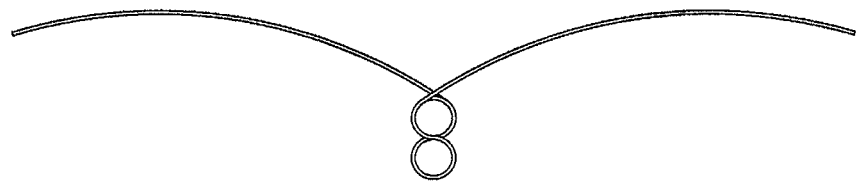
Figure 20J:
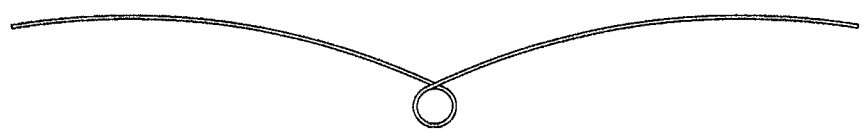
Figure 20K:
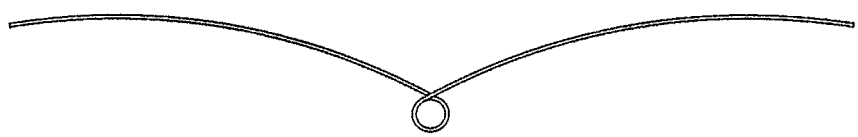
Figure 21:
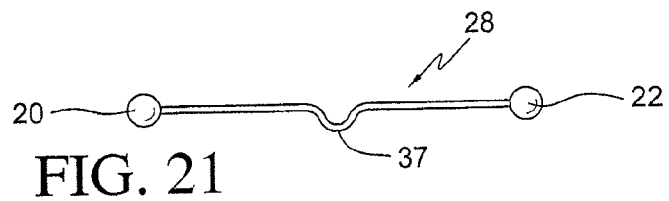
FIGS. 21-25 show alternate embodiments employing a substantially straight elongated member.

In accordance with yet another embodiment and as shown in FIG. 19, a biased loop 39 composed of multiple windings may also be employed. Similarly, and with reference to FIGS. 20A-20K, the biased loops 39 may take a variety of configurations designed to achieve a desired bias along the length of the first and second legs 34, 36. Ultimately, the bias of the connection member may be varied to suit the specific needs of the user.

Considering the various shapes that may be employed in accordance with a preferred embodiment of the present invention, it is contemplated the outward bias of the first and second legs may be achieved by creating resilience along the length of the first and second legs rather than at the connection point of the first and second legs. For example, where the first and second legs are formed of Nitinol, the first and second legs may be formed such that they bow outwardly when exposed to elevated activation temperature upon placement within the body.

With regard to the material construction of the elongated member 28, and further to the earlier disclosure, it is preferably composed of resilient, biocompatible materials (metal, polymer or composite) or shape memory or super-elastic materials (for example, Nitinol), other alloys, or combinations thereof, capable of offering the biasing characteristics discussed herein and required for proper operation of the present invention. If a material desired for use is not biocompatible, it could be covered by another biocompatible material, for example, a coating or a thin-walled plastic tube.

Further to the various shapes in which the elongated member 28 may be formed as disclosed above, other shapes are shown with reference to FIGS. 21 to 25. In accordance with these various embodiments, the elongated member 28 could be normally straight when unbiased and positioned within the uterine cavity 16. In accordance with this embodiment, the elongated member 28 would be forcibly folded inside the delivery container 48 (as discussed below in greater detail). The elongated member 28 is folded in this configuration until such a time that it is introduced within the uterine cavity 16 and released for positioning in a manner biasing the lateral walls 15a of the uterine cavity 16 outwardly. Upon deployment, the elongated member 28 extends to an angular configuration with the plug members 20, 22 positioned along the lateral walls 15a of the uterine cavity 16. It should be appreciated the angle is variable, and depends on the size of the uterus. The angle is usually around 90 degrees or so, but varies significantly.

Figure 22:
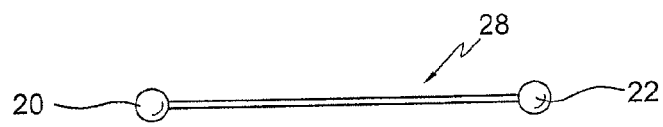
Figures 23, 24:
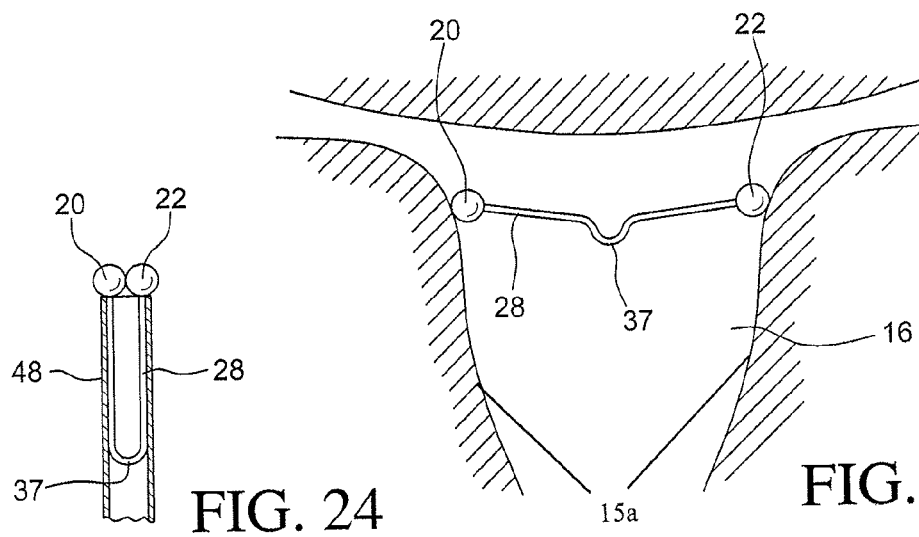
Figure 25:
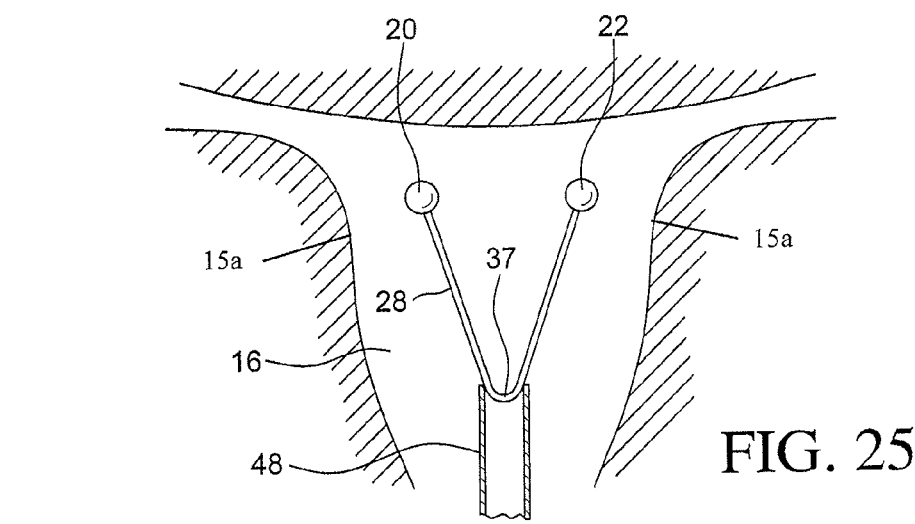

Referring to FIGS. 21 and 23-25, the elongated member 28 could be formed with a U-shaped connection member 37. The connection member 37 is shaped and dimensioned for facilitating the folding and positioning of the elongated member 28 within the delivery container 48 for subsequent expansion thereof when the elongated member 28 is released during application within the uterine cavity 16. The connection member 37 also allows for control of the resilience imparted to the elongated member 28 in accordance with desired parameters. FIG. 22 shows an embodiment wherein the connection member 37 is continuous with the elongated member.

Figure 26A:
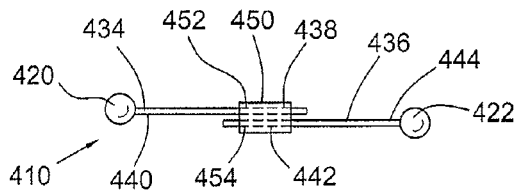
FIGS. 26A, 26B and 26C show an alternate structure for an intrauterine device in accordance with the present invention.
Figure 26B:
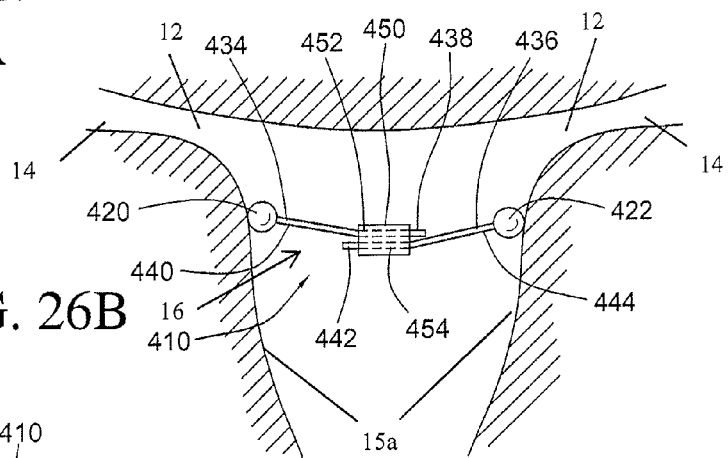

As discussed above, other mechanical mechanisms for the application of the plug members to the walls 15a of the uterine cavity 16 are contemplated. For example, mechanical force generating structures may be employed within the spirit of the invention. With this in mind, and with reference to FIGS. 26A, 26B and 26C, the intrauterine device 410 includes an elongated member 428 composed of first and second legs 434, 436 connected to each other for controlled relative movement by a clamping member 450. More particularly, the intrauterine device 410 is composed of first and second legs 434, 436, each of the first and second legs 434, 436 includes a first end 438, 442 and a second end 440, 444 wherein an plug member 420, 422 is secured to the respective second ends 440, 444 of the first and second legs 434, 436 and the respective first ends 438, 442 are secured via the clamping member 450.

The clamping member 450 is a generally elongated member including first and second apertures 452, 454 shaped and dimensioned for receiving the respective first ends 438, 442 of the first and second legs 434, 436. Until the clamping member 450 is crimped to lock the first and second legs 434, 436 in position relative to the clamping member 450 (as will be discussed below in greater detail), the apertures 452, 454 are formed to permit relative movement of the first and second legs 434, 436, and ultimately, the first and second plug members 420, 422, as the first and second legs 434, 436 are moved within the clamping member 450. As will be appreciated based upon the figures, the first and second legs 434, 436 are formed from slightly flexible materials allowing for bending thereof so as to conform to the anatomical distinctiveness of each individual patient.

Figure 26C:
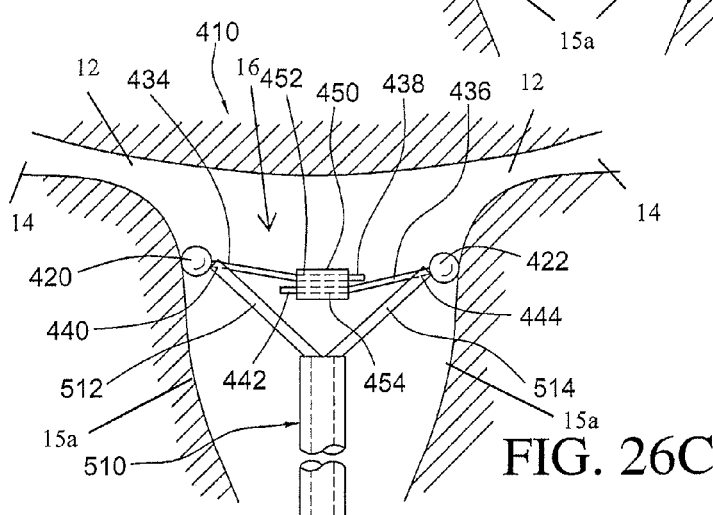

In accordance with a preferred embodiment, deployment of the intrauterine device 410 is facilitated through the utilization of a deployment assembly 510 as shown with reference to FIG. 26C. The deployment assembly 510 includes first and second members 512, 514 which are resiliently biased outwardly to engage and force the plug members 420, 422 into the walls of the uterine cavity 16. The deployment assembly 510 is further provided with a force gauge 516 for measuring the applied pressure as the plug members 420, 422 are forced outwardly into contact with the lateral walls 15a of the uterine cavity 16. Alternatively, the deployment assembly could be equipped with a force indicator such as a colored slide that moves to another position when appropriate pressure is achieved.

In practice, the intrauterine device 410 is delivered to the uterine cavity 16 and roughly positioned in the upper part of the uterine cavity 16 and deployed there. It then uses the shape of the uterine cavity 16 as a guide and positions itself in the uterine cavity 16 such that the plug members 420, 422 push slightly against the uterine walls 15a at a position adjacent the orifices 12 of the fallopian tubes 14 distorting it over time. In practice it has been found that complete migration and distortion is achieved over a period of a few weeks. The deployment assembly 510 is then employed to push the first and second plug members 420, 422 into contact with the lateral walls 15a of the uterine cavity 16. When a desired application pressure is achieved, the clamp member 450 is crimped in a manner securing it to the first ends 438, 442 of the respective first and second legs 434, 436 thereby locking the first and second legs 434, 436 in position relative to each other. Crimping of the clamping member 450 is achieved through utilization of medical grade forceps shaped and dimensioned to access the uterine cavity 16 and engage the clamping member 450.

Figure 27:
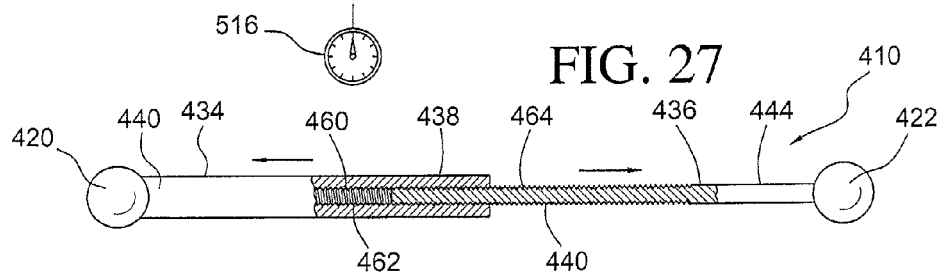
FIG. 27 shows yet another structure for an intrauterine device in accordance with the present invention.

In accordance with another embodiment as shown with reference to FIG. 27, an elongated member 428 composed of first and second legs 434, 436 is similarly provided. The first and second legs 434, 436 respectively include first and second plug members 420, 422 secured to the second ends 440, 444 thereof. The first ends of the first and second legs 434, 436 are structured for a telescopic mating relationship. In particular, the first end 438 of the first leg 434 includes a central threaded passageway 460 shaped and dimensioned for receiving the first end 442 of the second leg 436 in a threaded mating configuration. With this in mind, the internal cavity of the central threaded passageway 460 of the first leg 434 includes threading 462 shaped and dimensioned to mate and engage threading 464 formed along the external surface of the second leg 436. As such, rotation of the first and second legs 434, 436 relative to each other alters the effective length of the intrauterine device 410 by moving the first and second plug members 420, 422 further apart.

In practice, the intrauterine device 410 is delivered to the uterine cavity 16 and roughly positioned in the upper part of the uterine cavity 16 and deployed there. It then uses the shape of the uterine cavity 16 as a guide and positions itself in the uterine cavity 16 such that the plug members 420, 422 push slightly against the uterine wall 15a distorting it over time. In practice it has been found that complete migration and distortion is achieved over a period of a few weeks. The first and second legs 434, 436 are then engaged and rotated, pushing the first and second plug members 420, 422 outwardly into contact with the lateral walls 15a of the uterine cavity 16. When a desired application pressure is achieved, rotation is terminated thereby locking the first and second legs 434, 436 in position relative to each other with the plug members 420, 422 positioned such that they apply outward pressure to the lateral walls 15a of the uterine cavity 16.

Figure 28:
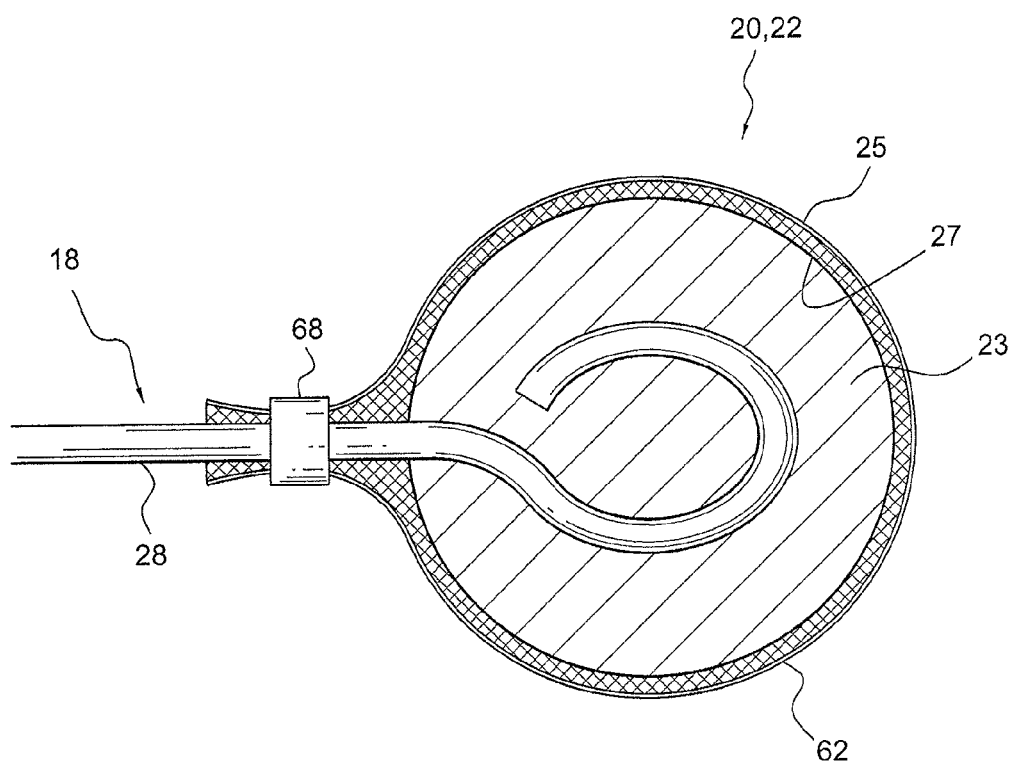
FIG. 28 is a cross sectional view of a plug member in accordance with a preferred embodiment of the present invention.

As shown with reference to FIGS. 3-6, 7A-D and 8-11, and in accordance with a preferred embodiment, the plug members 20, 22 are spherical. In accordance with a preferred embodiment, the plug body 23 of the plug member 20, 22 is made of silicone or porous, high density polyethylene exhibiting structure permitting tissue in-growth. Depending upon whether it is desired to provide a retrievable plug member 20, 22 or a permanently anchored plug member 20, 22, the outer surface 25 of the plug member 20, 22 will either be the silicone from which it is made (in which case the plug body 23 forms substantially all of the plug member 20, 22 as shown in FIGS. 3-6, 7A-D and 8-11), be composed of a tissue in-growth member 62, for example, porous, high density polyethylene, which is secured about the outer surface 27 of the silicone plug body (or substrate) 23 (see FIG. 28 which is discussed below in greater detail), or be composed of a foamed silicone with interstitial voids.

Where a permanent anchoring of the plug member 20 is desired, and with reference to an embodiment of the present invention as disclosed with reference to FIG. 28, a tissue in-growth member 62 is positioned over the silicone substrate material making up the plug body 23 so as to provide the plug member 20, 22 with an outer tissue in-growth surface 27. Although reference numeral 20 is used in describing the plug member it will be understood the first and second plug members 20, 22 are identical and/or symmetric. However, it is contemplated it may be advantageous to provide for an asymmetric construction with the first and second plugs differing in construction.

The tissue in-growth member 62 is constructed of a material promoting and maintaining tissue in-growth for the purpose of anchoring the plug member 20 and/or creating a seal. It is contemplated the tissue in-growth member 62 could be a biocompatible fabric (for example, a polyester fabric), textile, felt or membrane known by those skilled in the art to encourage tissue in-growth. In accordance with a preferred embodiment of the present invention, it is contemplated the tissue in-growth member 62 may be a knitted polymer textile with appropriate tissue in-growth properties to be considered an acceptable option for use in conjunction with the present invention. The tissue in-growth member could further be covered with a specialty coating that enhances and/or accelerates tissue in-growth.

The tissue in-growth member 62, which is also referred to as a "fabric sock" in accordance with the embodiments described below, may be secured to the plug body 23 through the implementation of various techniques. For example, and with reference to FIG. 29, a cylindrical fabric sock 62 with open ends is placed over the plug body 23 and the fabric sock 62 is twisted so as to create a reduced diameter by twisting or knotting, section 64 distal of the plug body 23. Thereafter, the distal portion 66 of the fabric sock 62 is pulled proximally and over the reduced diameter twisted section 64 and the plug body 23. A band 68 is then applied to the fabric sock 62 proximally of the plug body 23 to secure it in position about the plug body 23.

In accordance with an alternate embodiment, and with reference to FIG. 30, a fabric sock 62 with a closed distal end 70 is pulled over the plug body 23. The closed distal end 70 is preferably formed through the application of heat to close the distal end 70 of the fabric sock 62. Once the fabric sock 62 is pulled over the plug body 23 with the closed distal end 70 of the fabric sock 62 covering the distal end of the plug body 23, the proximal end 72 of the fabric sock 62 is closed via the application of a band 68 proximally of the plug body 23 to secure it in position about the plug body 23.

In accordance with yet another embodiment, and with reference to FIG. 31, a cylindrical fabric sock 62 with open ends may be formed into a double layered, closed ended fabric sock 62 by tying the center 74 of the cylindrical fabric sock 62 and pulling one end 76 thereof over the other end 78 resulting in a fabric sock 62 with a closed distal end 70. Thereafter, the fabric sock 62 is pulled over the plug body 23 with the closed distal end 70 of the fabric sock 62 covering the distal end of the plug body 23, the proximal end of the fabric sock 62 is closed via the application of a band 68 proximally of the plug body 23 to secure it in position about the plug body 23. The embodiment disclosed above with reference to FIG. 32 may be varied by utilizing a washer 80 to constrict the center of the cylindrical fabric sock 62 as opposed to the tie disclosed above.

Figure 33:
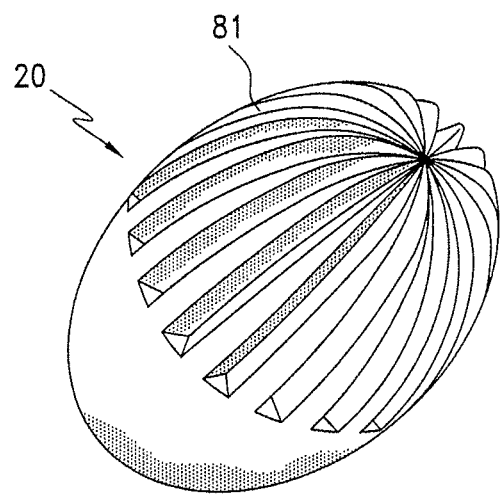
FIGS. 33 and 34 show plug members specifically designed for encouraging tissue in-growth.
Figure 34:
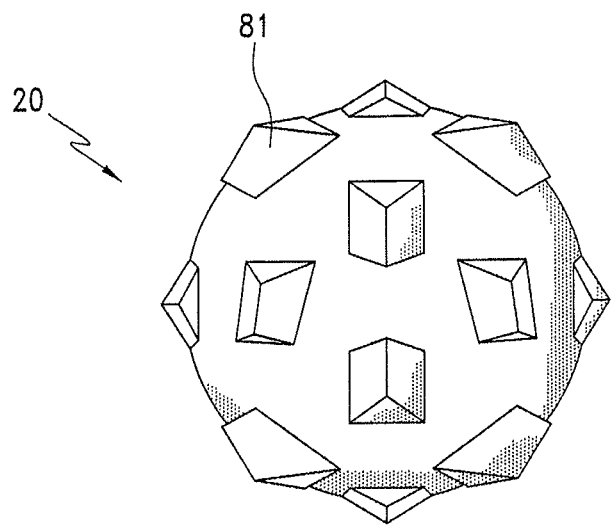

With reference to FIGS. 33 and 34, plug members with various in-growth promoting construction are disclosed. In accordance with FIG. 33, the plug member 20 is provided with grooves 81 to promote tissue in-growth. Such a concept might utilize plug members which are round, spherical, square, etc. In accordance with another embodiment as shown with reference to FIG. 34, the plug member 20 is provided with a spike or barb 81 designed to promote tissue in-growth.

Figure 35:
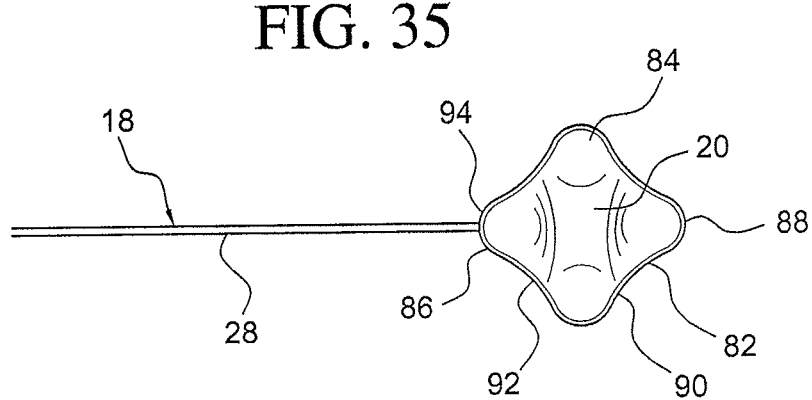
FIGS. 35 and 36 are top plan views showing alternate plug member shapes in accordance with the present invention.

Although a spherical plug member is disclosed above in accordance with a preferred embodiment, those skilled in the art will appreciate other shapes may be used without departing from the spirit of the present invention. Although reference numeral 20 is used in describing the plug member, it will be understood the first and second plug members 20, 22 are identical. In accordance with a first alternate embodiment, and with reference to FIG. 35, the plug member 20 takes the form of a "flying saucer". As such, the plug member 20 includes an upper conical surface 82 with a domed tip, a central portion 84, and a lower conical surface 86 with a domed tip. More particularly, the upper conical surface 82 is substantially cone-shaped with a concave wall and extends from a rounded crown section 88 to a wider base section 90 which transitions into the central portion 84. The central portion 84 is substantially circular in cross section with a convex wall and extends from a smaller top radius portion to a large central radius portion and back to a smaller bottom radius portion. Beneath the central portion 84 is the lower conical surface 86 that is a mirror image of the upper conical surface 82 and, therefore, extends from a relatively large radius base section 92 to a rounded crown section 94 at its lowest extent.

Figure 36:
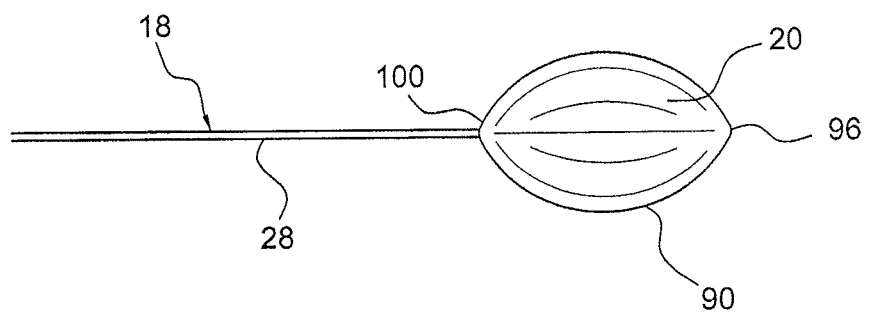

Referring to FIG. 36, a plug member 20 with a football shape is disclosed. This shape includes a convex outer wall and a circular cross section when viewed in a plane perpendicular to the longitudinal axis of the plug member 20 that goes from a relatively small radius first tip member 96 to a large radius central section 98 and back to a small radius second tip member 100.

Figure 37:
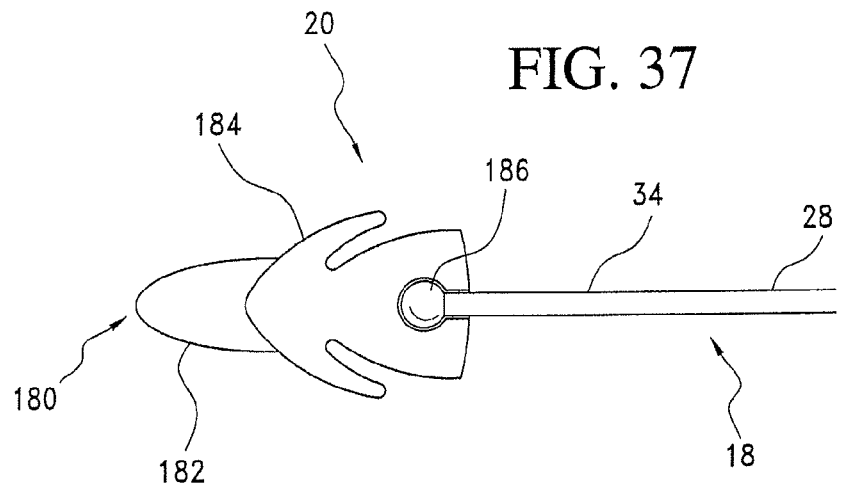
FIGS. 37, 38, 39, 40, 41, 42 and 43 are schematic views of alternate embodiments of a plug member and/or elongated member structure in accordance with the present invention.

Further, and with reference to FIG. 37, a ball and socket arrangement for a plug member 20 is disclosed. In accordance with such an embodiment, the plug member 20 is designed with a leading end 180 having a guiding nose 182 shaped and dimensioned to find the appropriate location along the wall of the uterine cavity 16. Articulation of the plug member 20 is achieved by coupling the plug member 184 to the first (and second) leg 34 via a ball joint 186. The ball and socket joint of this embodiment would provide the plug member 20 with a degree of freedom to swivel and angularly align with the walls 15a of the uterine cavity 16 creating a more even distribution of force.

Figure 38:
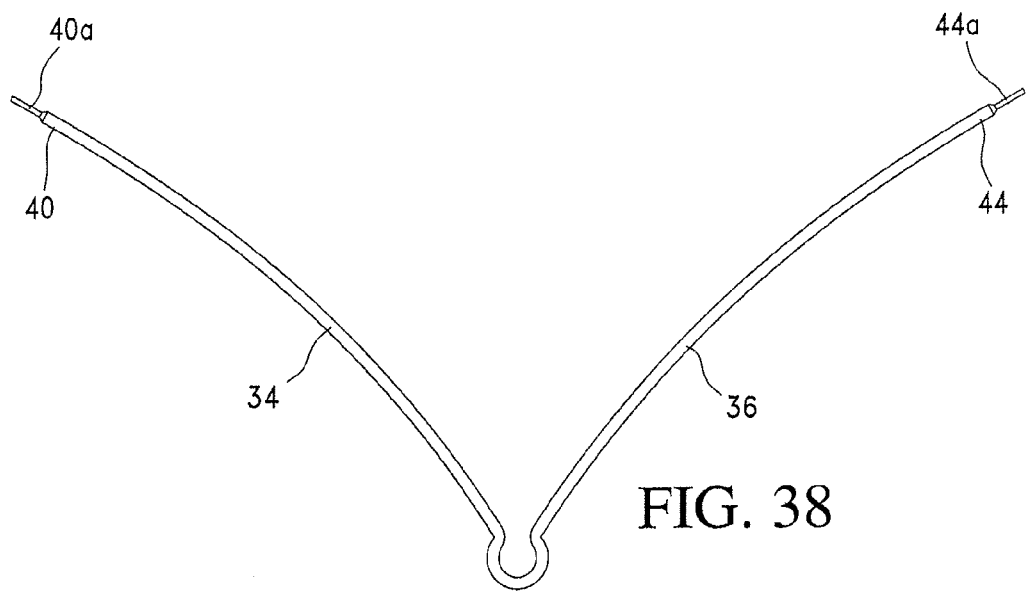
Figure 39:
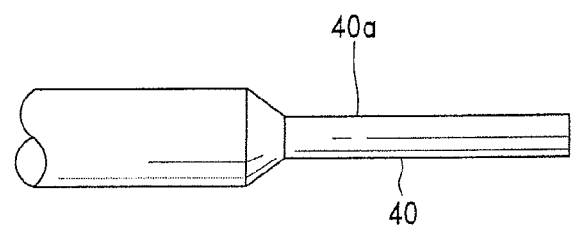

In accordance with an alternate embodiment, and with reference to FIGS. 38 and 39, a flexibility similar to the ball and socket arrangement may be achieved by reducing the cross sectional area at the second ends 40, 44 of the respective first and second legs 34, 36 to achieve a higher flexibility and improved compliance to the uterine cavity shape. As a result, the second ends 40, 44 at each of the respective first and second legs 34, 36 are provided with a reduced diameter section 40a, 44a allowing for greater flexibility of the elongated member 28 in the area adjacent the first and second plug members 20, 22.

Figure 40:
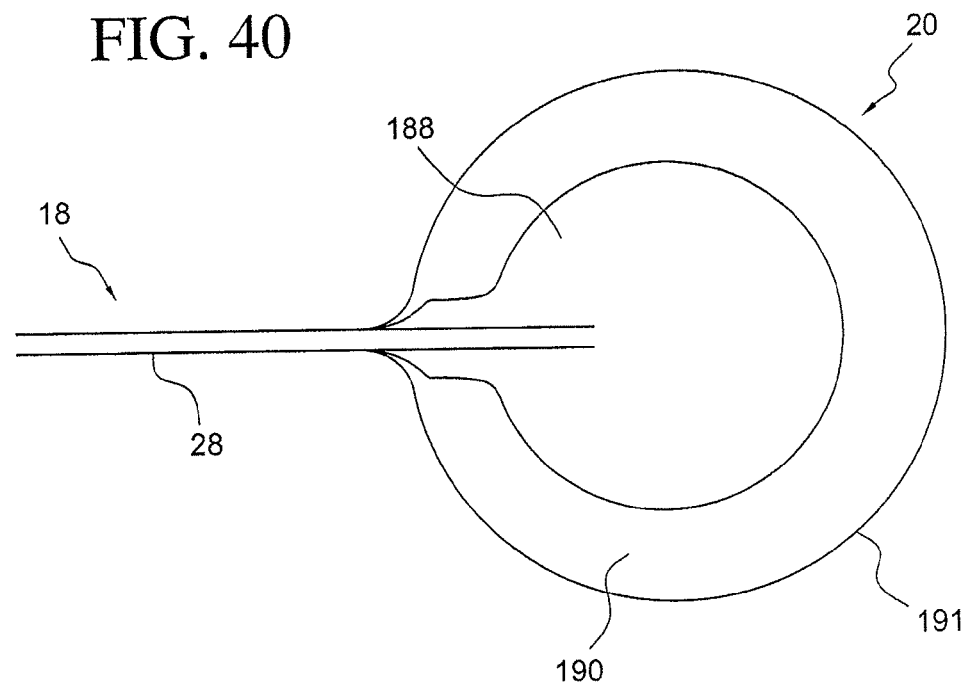

As discussed above, the plug members are composed of porous polyethylene in accordance with a preferred embodiment. However, and for each of the plug shapes disclosed above, the plug members may be formed in a dual density configuration of various biocompatible elastomers. In particular, and with reference to FIG. 40, the inner portion 188 of the plug member 20 is made from a relatively hard material and forms a foundation for the plug member 20. Affixed over the inner portion 188 is an outer soft pliable material 190. The soft pliable material 190 forms the outer surface 191 of the plug member 20.

Figure 41:
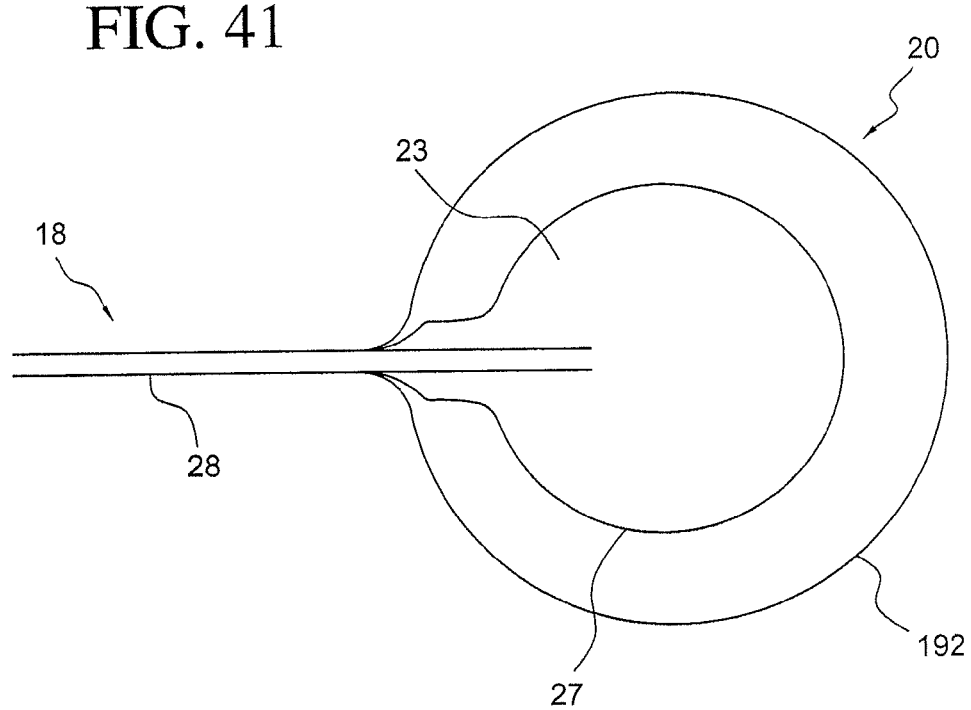

In accordance with an alternate embodiment, and with reference to FIG. 41, the plug member 20 maybe formed with a hard outer shell 192 (for example, gelatin tablet material) temporarily affixed to the outer surface 27 of the main plug body 23 of the plug member 20 that is made of a soft pliable material (or a dual density configuration as described above) for the purpose of protecting the softer inner material. The hard outer shell 192 behaves like a slippery surface during insertion and deployment. However, the hard outer shell 192 is composed of a bioabsorbable or decomposable (that is, expelled during normal menstrual cycle) material which quickly dissolves upon deployment within the uterine cavity 16. As a result, the hard outer shell 192 dissolves and is discharged or absorbed allowing the soft pliable material of the outer surface 27 to ultimately seat along the lateral walls 15a of the uterine cavity 16.

Figure 42:
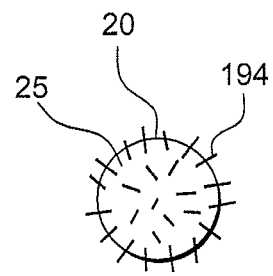
Figure 43:
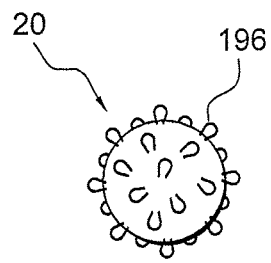

As discussed above in accordance with a preferred embodiment, enhanced coupling of the plug member to the tissue surface is achieved by the application of a tissue in-growth member of mesh about the silicone outer surface of the plug member. However, it is contemplated other techniques may be employed to achieve desirable coupling of the plug member along the wall of the uterine cavity. For example, and in accordance with one embodiment as shown with reference to FIG. 42, the outer surface 25 of the plug member 20 is provided with tissue in-growth promoting/compatible whiskers 194. The tissue in-growth promoting/compatible whiskers 194 help to integrate the plug member 20 within the anatomy. Similarly, and with reference to FIG. 43, tissue in-growth promoting/compatible loops 196 may be integrated into the plug member 20 for the same purpose of securing the same to the anatomy. Where such tissue in-growth promoting structures are employed, they may be composed of bioresorbable or bioabsorbable materials such that the plug members will completely dissolve over a predetermined period of time or they may simply be composed of tissue in-growth promoting materials that will remain stable until such a time the plug members are removed.

Figure 6:
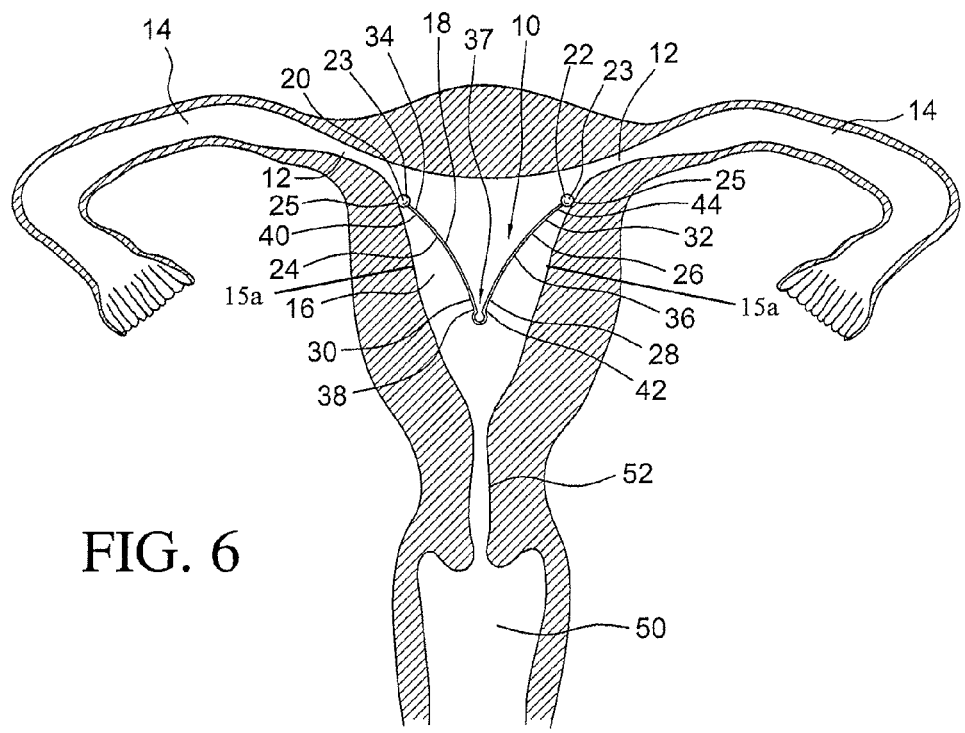
Figure 46:
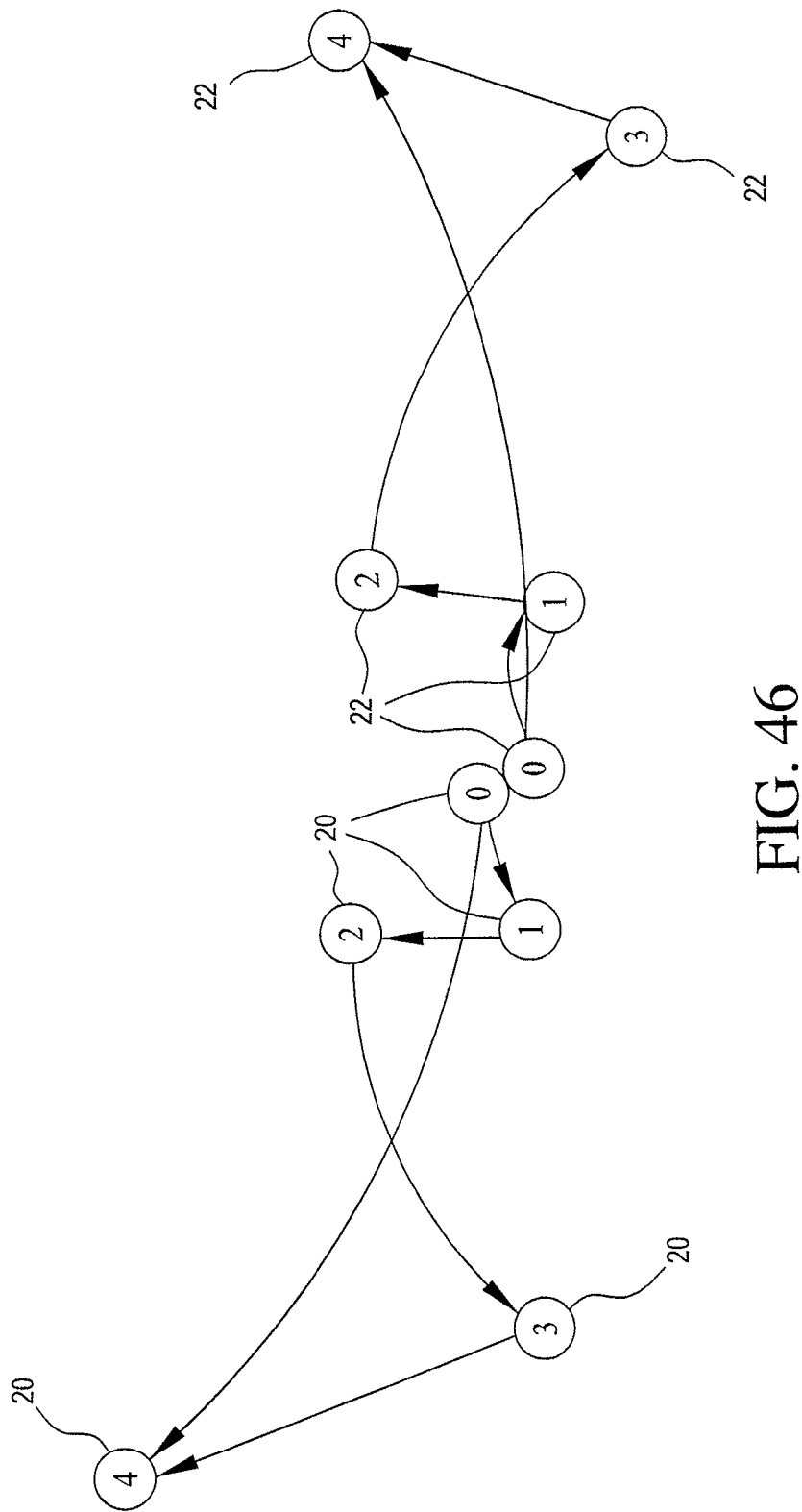
FIG. 46 is a schematic demonstrating movement of the plug members during deployment of the intrauterine device shown with reference to FIGS. 1-13.

Delivery of the present intrauterine device is achieved in the manner described with reference to commonly owned PCT Publication No. WO2006/088909, which is based upon International Application No. PCT/US2006/005245, filed Feb. 15, 2006, entitled "INTRAUTERINE FALLOPIAN TUBE OCCLUSION DEVICE AND METHOD FOR USE", which is incorporated herein by reference. Briefly, and with reference to FIGS. 1 to 6 and 46, the intrauterine device 10 is packaged in a small caliber longitudinal delivery container 48 which forms part of the delivery apparatus 46. This delivery container 48 is advanced into the uterine cavity 16 through the vagina 50 and cervix 52 (FIG. 2 and Points 0 of FIG. 46 which show the position of the plug members 20, 22 at this step of the deployment). Once inside the uterine cavity 16, the intrauterine device 10 is partially released and advanced from the delivery container 48 via a delivery rod 54 extending through the delivery container 48 for pushing the intrauterine device 10 from its storage position within the delivery container 48, preferably, while pulling the delivery container (or sheath) 48 back so as to prevent damage to the uterus or intrauterine device 10. Upon initial deployment, the plug members 20, 22 will first move outwardly due to the stored outward bias in the first and second legs 34, 36 (see Points 1 of FIG. 46 which show the position of the plug members 20, 22 at this step of the deployment). As the intrauterine device 10 is further deployed, the plug members 20, 22, move upwardly within the uterine cavity 16 (see Points 2 of FIG. 46 which show the position of the plug members 20, 22 at this step of the deployment). Once the intrauterine device 10 is fully or almost fully released from the delivery container 48 during deployment, with the present intrauterine device 10 no longer being contained by the delivery container 48 (with the delivery rod 54 secured thereto in accordance with a preferred embodiment), the first and second legs 34, 36 and the connection member 37 bow outwardly allowing the intrauterine device 10 to take a shape of a "Y" with the plug members 20, 22 in contact with respective opposed lateral walls 15a of the uterine cavity (FIG. 3 and Points 3 of FIG. 46 which show the position of the plug members 20, 22 at this step of the deployment)). As the intrauterine device 10 further opens with the first and second legs 34, 36 moving apart and the respective plug members 20, 22 applying pressure to the opposed lateral walls 15a of the uterine cavity 16, the plug members 20, 22 of the intrauterine device 10 ride up the opposed lateral walls 15a of the uterine cavity 16 directing themselves to a seating position along the lateral walls 15a of the uterine cavity 16 at a position adjacent the orifices 12 of the fallopian tubes 14 were they apply outward pressure to the lateral walls 15a of the uterine cavity 16 in a manner preventing conception (FIG. 4 and Points 4 of FIG. 46 which show the position of the plug members 20, 22 at this step of the deployment). At that point when the intrauterine device 10 can be compressed against the lateral walls 15a of the uterine cavity 16 it will be released (FIG. 5), whether manually or automatically, from the delivery apparatus 46. The delivery apparatus 46 will be removed and the present intrauterine device 10 will stay in place (FIG. 6). With the foregoing in mind, the present invention provides a device and system for implantation positioning whereby an appropriate combination of defined deployment displacement and elastic behavior position the implant's plug members along the walls of the uterine cavity.

Control of the applied force is important because the applied force, or pressure, causes irritation and encourages subsequent in-growth of tissue within an in-growth encouraging plug member (as disclosed herein) as the plug member contacts the lateral wall of the uterine cavity and/or the orifice of the fallopian tube. With this in mind, the deployed intrauterine device 10 is designed to apply pressure within the uterine cavity in a manner causing irritation and encouraging tissue in-growth into the first plug member and the second plug member. More particularly, testing has revealed the plug members must preferably span a distance of approximately 18 mm to approximately 54 mm depending upon the anatomical characteristics of the patient. The elongated member (regardless of the embodiment as described herein) is, therefore, capable of moving (for example, spreading based upon the inherent spring bias) to spread the first and second plug members from between approximately 18 mm and 54 mm apart. The present intrauterine device, in particular, the elongated member, must further be capable of applying a relatively consistent force (for example, a load of approximately 5 grams in accordance with a preferred embodiment) while the plug members are positioned anywhere within the desired span between the lateral walls of the uterine cavity. In accordance with a preferred embodiment, the load required for the application of the force necessary to encourage in-growth is preferably approximately 5 to 50 grams, and more preferably 15 to 30 grams, when such a load is applied for a period of 1 to 3 months. Each of the embodiments disclosed herein attempts to accommodate these requirements with the controlled application of force. For example, the embodiment described above with reference to FIGS. 1 to 6 is preferably manufactured from Nitinol which has been found capable of providing relatively consistent application of force across a wide range of plug member spans (see FIG. 45 showing the load profiles for Nitinol at various rod thicknesses). Irritation (and/or damage) encouraging tissue in-growth may be further facilitated by applying corrosive material to the surface of the plug member.

A proposed embodiment for the delivery apparatus 46 is illustrated in FIGS. 7A to 7D. This illustration shows the delivery apparatus 46 with its plug members 20, 22 arranged longitudinally within the delivery container 48. Because of the need to maintain the delivery container 48 in the lowest profile possible (the bigger the delivery system the more dilatation of the cervix is needed), the plug members 20, 22 are located, staggered, one in front of the other. This also means that the two legs 34, 36 of the intrauterine device 10 in this embodiment are a slightly different length. It is contemplated this staggered arrangement may be achieved by making one leg shorter than the other or by flexing or bending one of the legs to force a corresponding leg to stay behind the other. Although this embodiment employs a staggered arrangement, it is contemplated the legs may be oriented side by side.

Figure 9:
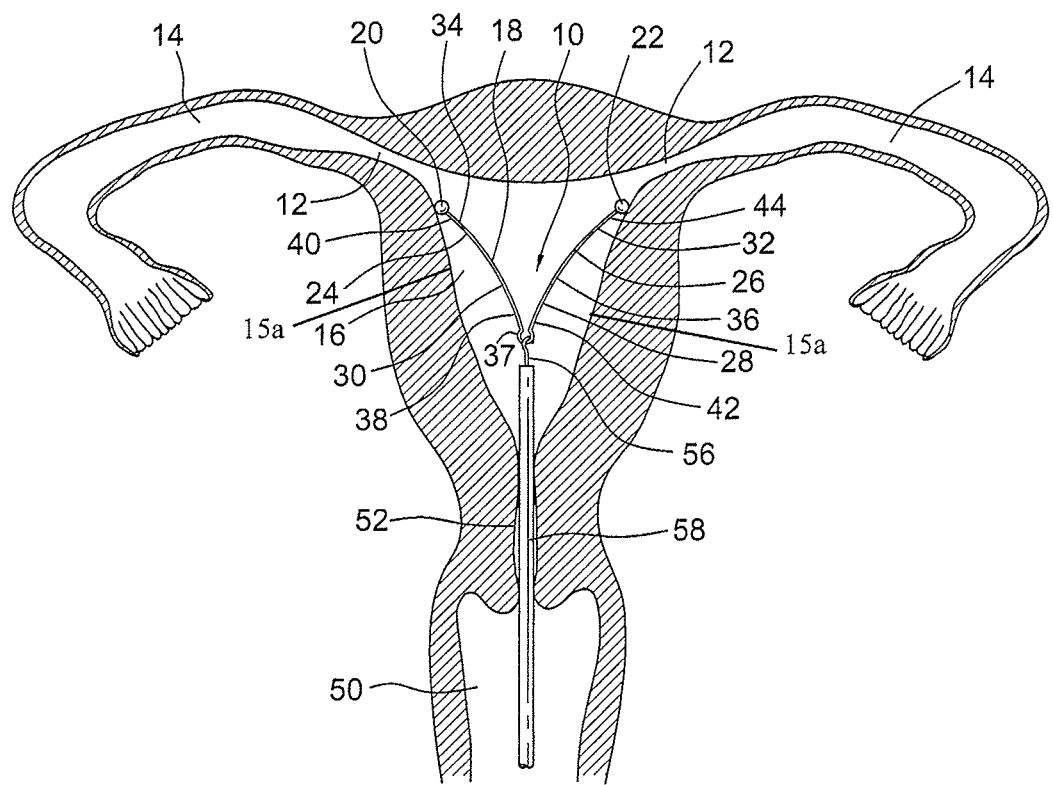
Figure 10:
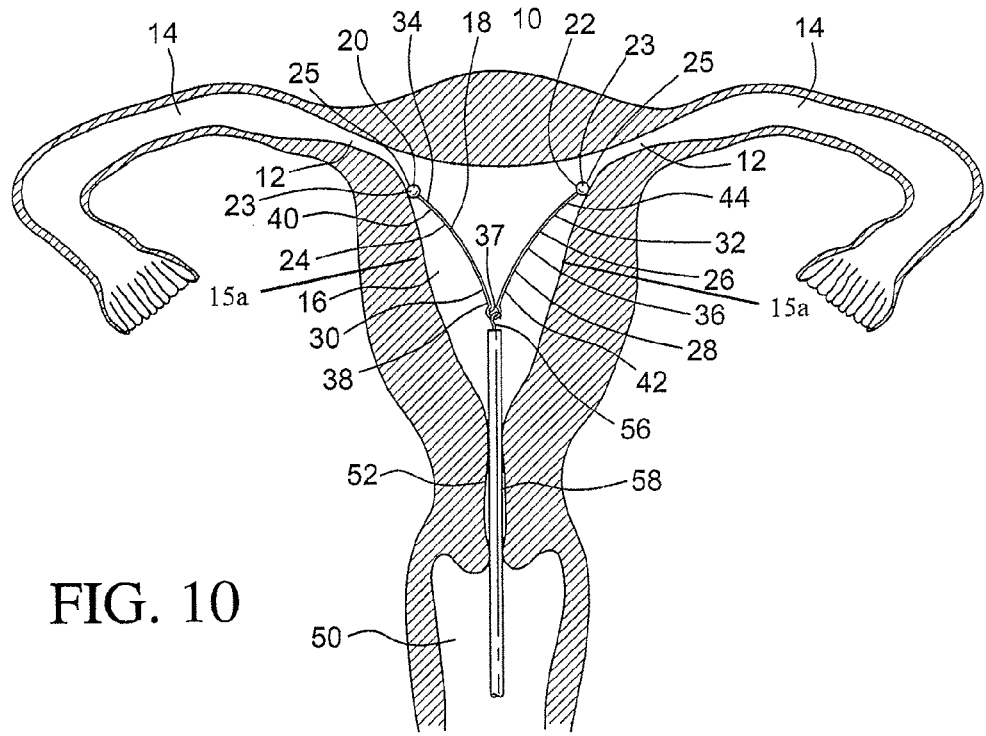
Figure 11:
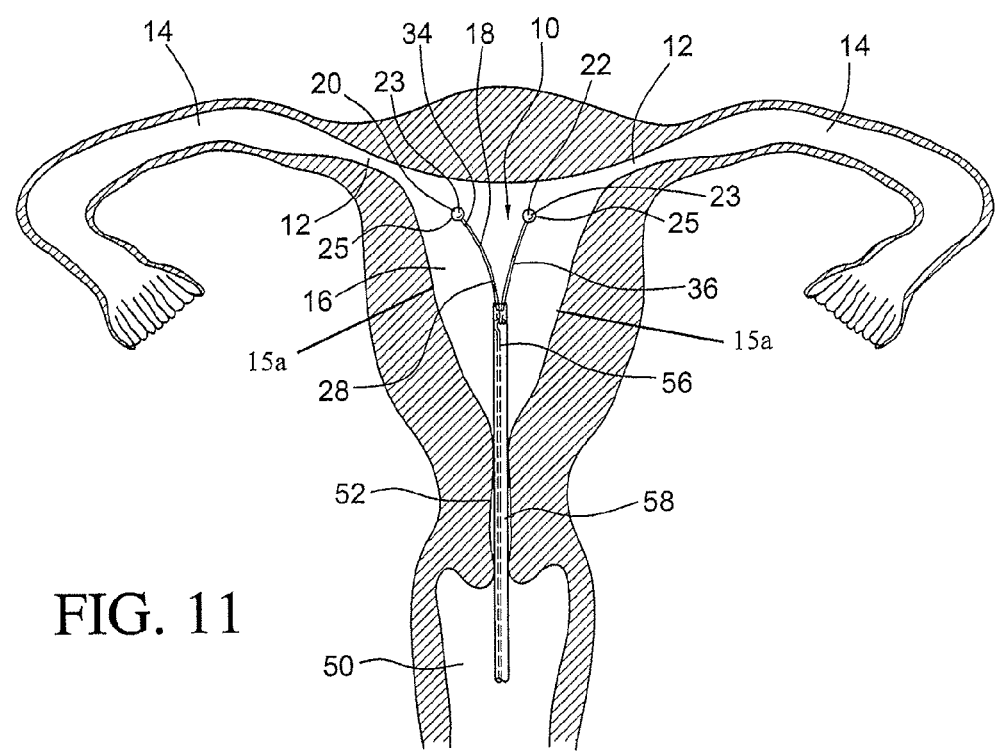
Figure 12:
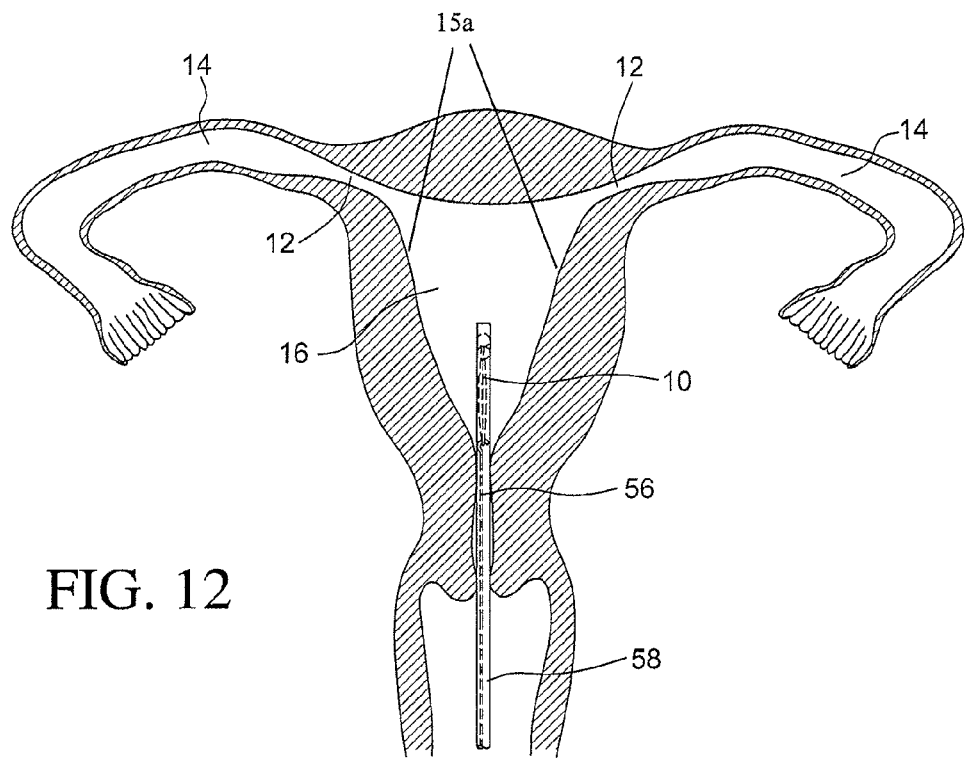
Figure 13:
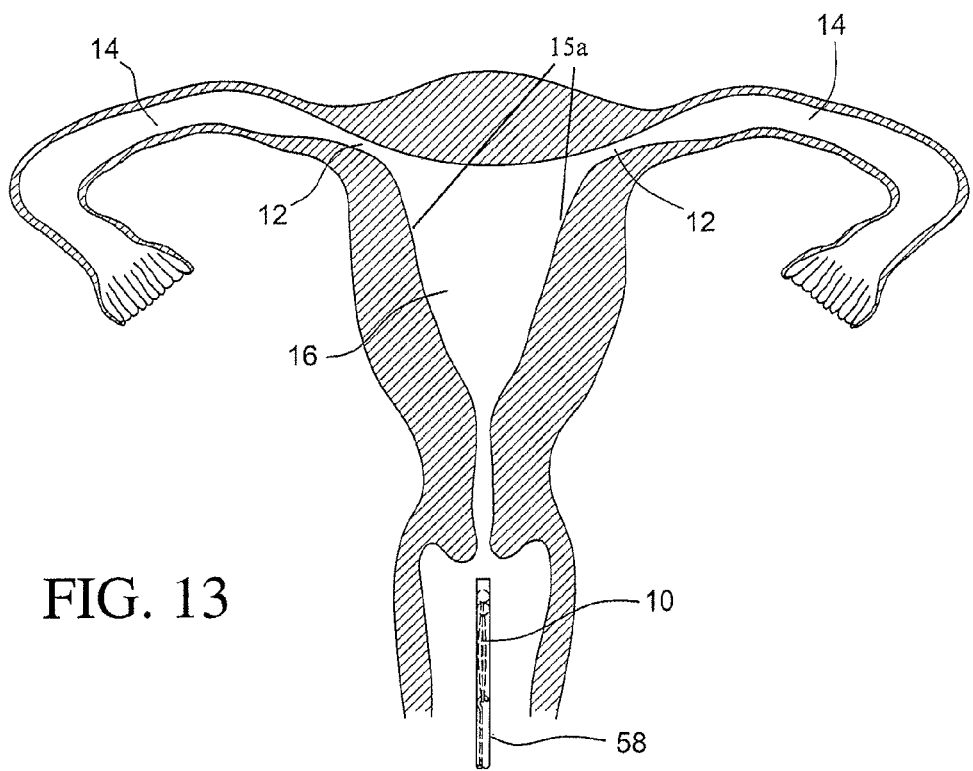

When removal of the intrauterine device 10 is desired, a hook 56, or other removal apparatus that engages the intrauterine device 10, will be advanced through the vagina 50 and cervix 52 (FIG. 8) and the connection point (for example, a metallic spring) between the plug members 20, 22 and the first and second legs 34, 36 will be grasped (FIG. 9). The hook 56 will pull on the intrauterine device 10 and insert it into a sheath 58 or into the hysteroscope (FIGS. 10, 11, 12). At that stage, the contained intrauterine device 10 is removed from the uterus and out through the cervix 52 and vagina 50 (FIG. 13). This removal would be done either with or without direct visualization or under fluoroscopic guidance.

Figure 8:
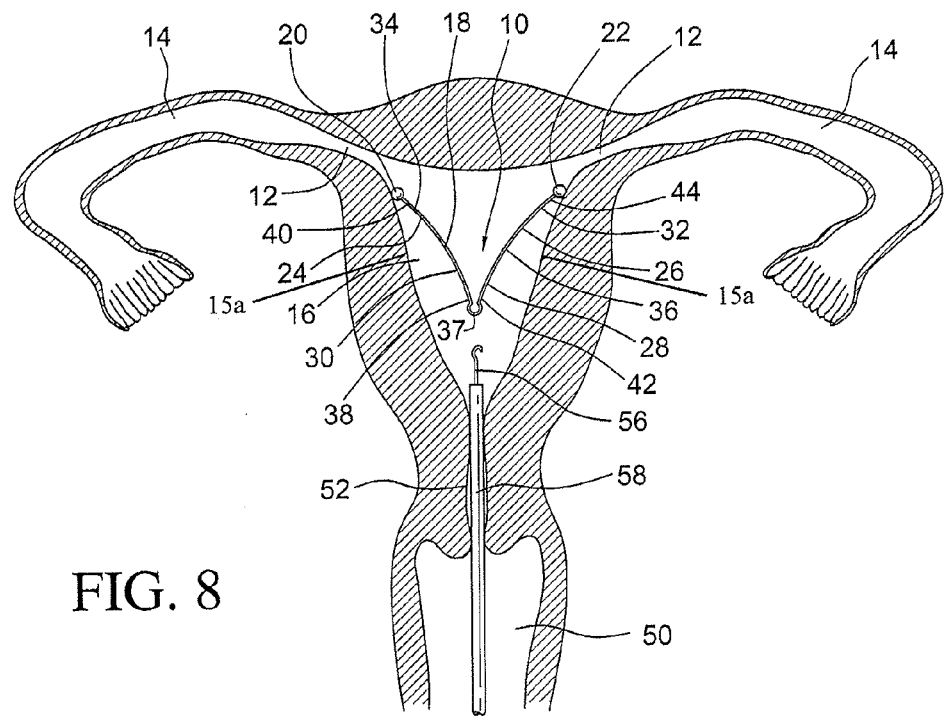
Figure 8A:
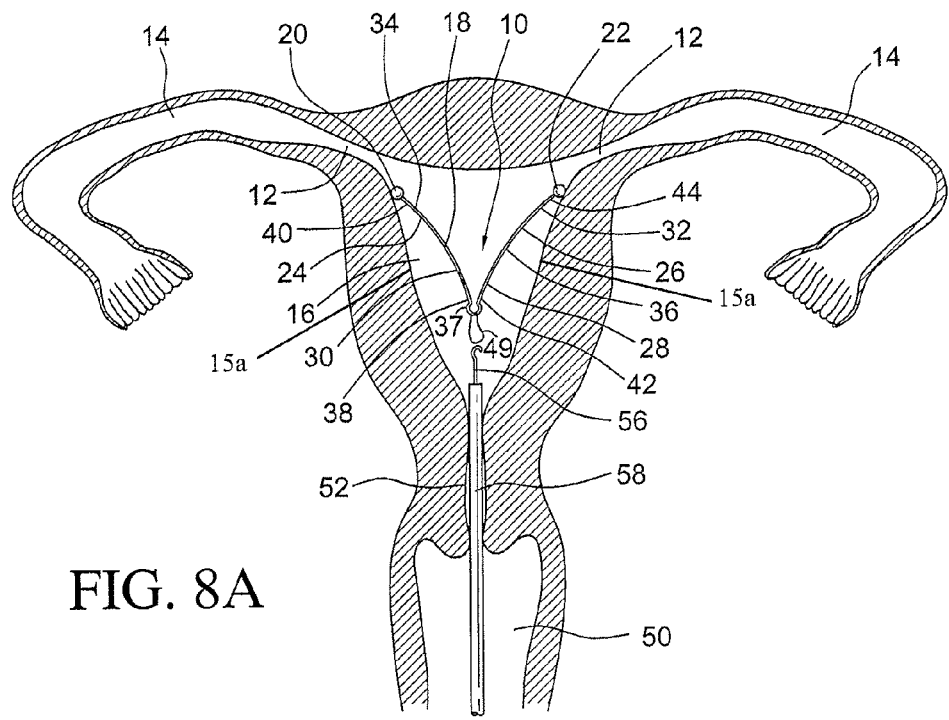
FIG. 8A shows an alternate embodiment in accordance with the present invention.

In accordance with an alternate embodiment and with reference to FIG. 8A, a suture/string loop 49 may be secured to the connection member 37. As such, either the hook 56 or other engagement device may grab the suture/string loop 49 for retrieval of the intrauterine device.

Figure 47:
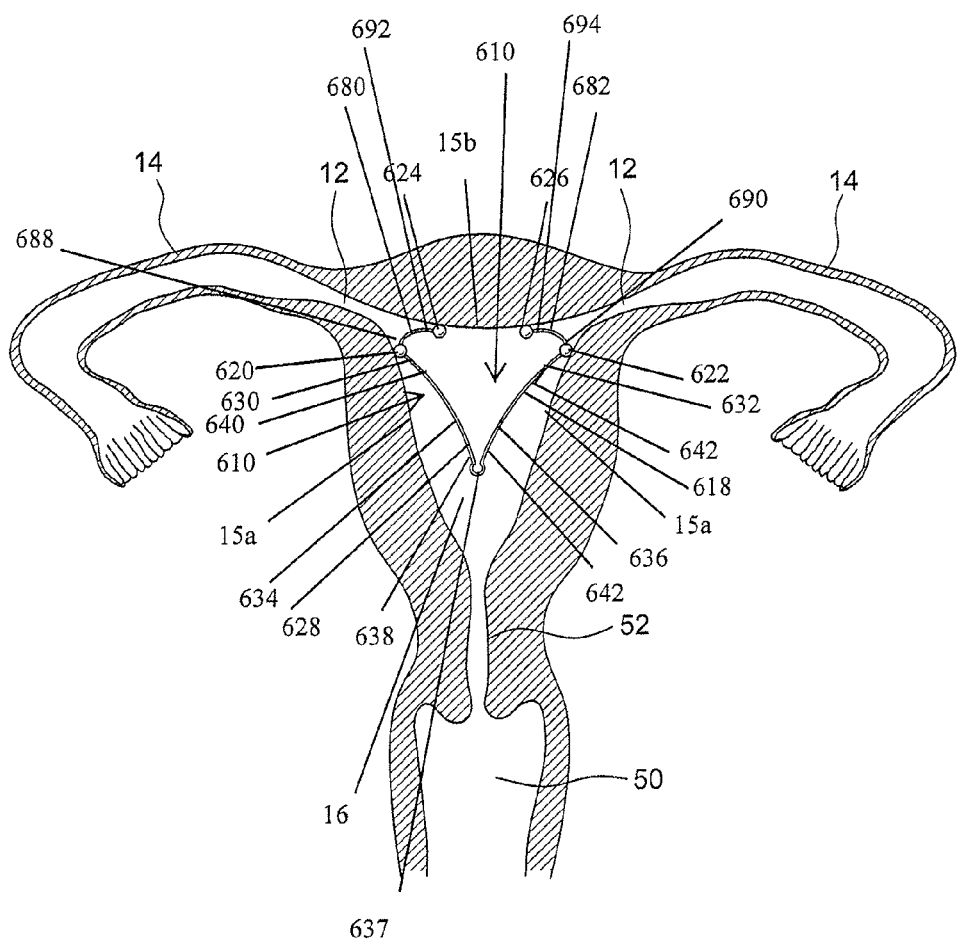
FIG. 47 is a schematic of an alternate embodiment in accordance with the present invention.

With reference to FIG. 47, an alternate embodiment of the present intrauterine device 610 is disclosed. As with the prior embodiments, the intrauterine device 610 includes a resilient body 618 having first, second, third and fourth plug members 620, 622, 624, 626 secured at strategic positions thereon. The resilient body 618 is shaped and dimensioned to expand in a substantially V-shape as disclosed with the prior embodiments. However, and in contrast to the prior embodiments, the resilient body 618 of the intrauterine device 610 includes resilient first and second extension arms 680, 682 respectively extending beyond the first and second plug members 620, 622, as well as the first and second legs 634, 636 for bearing against the upper wall 15b of the uterine cavity 16. In particular, the first and second extension arms 680, 682 are substantially C-shaped with inwardly facing concave surfaces. Accordingly, and when the first and second plug members 620, 622 are positioned against the lateral walls 15a of the uterine cavity 616, the free ends of the extension arms 680, 682 are oriented to bear against the upper wall 15b of the uterine cavity 16.

Enhanced application of pressure to the upper uterine wall 15b is achieved by providing the free ends of the extension arms 680, 682 with respective third and fourth plug members 624, 626. As with the prior embodiment, these plug members 624, 626 are substantially spherical and preferably manufactured from POREX porous polyethylene.

As with the prior embodiments, the first and second legs 636, 638 of the resilient body 618, as well as the first and second extension arms 680, 682 exhibit spring like characteristics. With this in mind, the resilient body 618 includes an elongated member 628 having a first end 630 and a second end 632. The first end 630 of the elongated member 628 is composed of the first leg 634 and first extension arm 680 and the second end 632 of the elongated member 628 is composed of the second leg 636 and the second extension arm 682. The first plug member 620 is secured at the distal end of the first leg 634 midway along the length of the first end 630 of the elongated member 628 and the second plug member 622 is secured at the distal end of the second leg 636 midway along the length of the second end 632 of the elongated member 628.

More particularly, the first leg 634 includes a first end 638 and a second end 640, and the second leg 636 includes a first end 642 and a second end 644. The first ends 638, 642 of the respective first and second legs 634, 636 are respectively connected, while the second ends 640, 644 of the first and second legs 634, 636 are respectively provided with the respective first and second plug members 620, 622 and coupled to the first and second extension arms 680, 682.

A connection member 637 resiliently couples the first ends 638, 642 of the first and second legs 634, 636 in a manner biasing the second ends 640, 644 of the first and second legs 634, 636, as well as the first end 630 and second end 632 of the elongated member 628, from each other when they are not restrained in a manner discussed below in greater detail.

The first leg 634 and the second leg 636 are angularly oriented relative to each other creating an elongated member 628 which is substantially V-shaped when the first leg 634 and the second leg 636 are allowed to move away from each other based upon the outward bias inherent in the connection member 637 between the first and second legs 634, 636. The inherent bias in the connection members 637 is created through the utilization of spring materials or shape memory materials in the construction of the resilient body 618, in particular, the connection member 637.

With this in mind, the connection member 637 preferably includes a substantially circular configuration with a first end 637a connected to the first end 638 of the first leg 634 and a second end 637b connected to the first end 642 of the second leg 636. The connection member 637 is formed with an inherent outward bias that forces the first leg 634 and the second leg 636 outwardly upon deployment.

In addition, and in accordance with the preferred embodiment, the first leg 634 and second leg 636 are formed with an outward bow when fully extended. This outward bow stores further outward bias when the intrauterine device 610 is compressed for storage and deployment.

As discussed above, first and second extension arms 680, 682 are secured to the second ends 640, 644 of the first and second legs 634, 636 such that they extend beyond the first and second plug members 620, 622. Each extension arm 680, 682 includes a first end 688, 690 secured to the second end 640, 644 of the first or second leg 634, 636 and a free second end 692, 694. The free second ends 692, 694 are respectively provided with third and fourth plug members 624, 626.

As discussed above, each of the first and second extension arms 680, 682 is formed with a resilient bias urging the first end 688, 690 and second end 692, 694 (that is, increasing the radius of curvature of the arc defined by the first and second extension arms 680, 682) thereof apart when the intrauterine device 610 is positioned within the uterine cavity 16. While the first leg 634 and second leg 636 exhibit an outward bow, that is, convex inner surfaces facing each other when the intrauterine device 610 is deployed, the first and second extension arms 680, 682 are exactly the opposite with their concave surfaces facing each other when deployed within the intrauterine cavity 16.

The present device offers a variety of other uses. These uses include applications for contraception, either temporary or permanent; especially for women who do not use IUDs because of the "post fertilization-embryo destruction" mechanism associated with the IUD's birth control. The present intrauterine device may also be used by women who do not wish to undergo a tubal ligation surgery.

Figure 44:
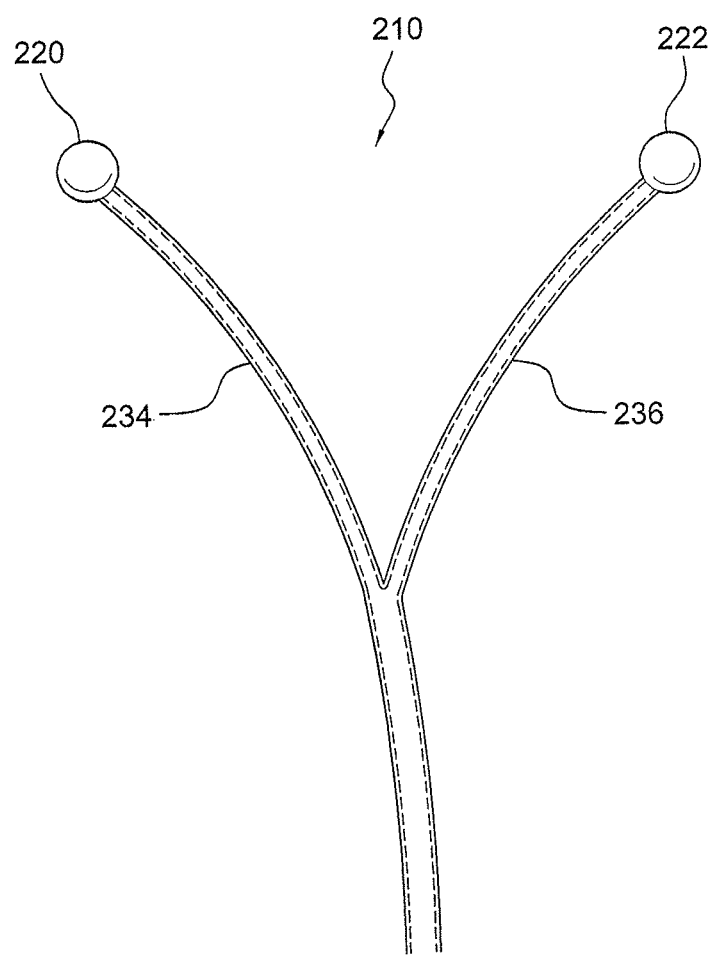
FIG. 44 is a schematic view of an alternate embodiment of an intrauterine device in accordance with the present invention.

In accordance with an alternate embodiment and with reference to FIG. 44, the intrauterine device 210 is provided with an elongated member 218 having hollow, tubular first and second legs 234, 236 allowing for the transport of an injectable material to the plug members 220, 222. As such, and in accordance with this embodiment, the plug members 220, 222 are made of a material (for example, a porous material) allowing transport of the injectable material from the first and second legs 234, 236, through the plug members 220, 222 and to the selected tissue.

As those skilled in the art will certainly appreciate, a variety of embodiments have been disclosed above for implementation of the present invention. These various embodiments may be utilized alone or in combination, and various features may be combined to achieve results remaining within the spirit of the present invention.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An intrauterine device for applying pressure to lateral walls of a uterine cavity, the intrauterine device comprising:
   a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;
   a first plug member secured at the second end of the first leg and a second plug member secured at the first end of the second leg, the first and second plug members being shaped and dimensioned for bearing against the walls of the uterine cavity as the elongated member spreads outwardly with the first end and the second end moving apart;

wherein the first and second plug members respectively apply a force of at least 0.01 ft·lb to the lateral walls of the uterine cavity.

2. The intrauterine device according to claim 1, wherein the elongated member extends between a folded configuration when stored for deployment and a deployed configuration when the first and second plug members are positioned against the walls of the uterine cavity.

3. The intrauterine device according to claim 1, wherein the second end of the first leg includes a reduced diameter section allowing for greater flexibility in an area adjacent the first plug member, and the second end of the second leg includes a reduced diameter section allowing for greater flexibility in an area adjacent the second plug members.

4. The intrauterine device according to claim 1, wherein the first plug member and the second plug member are composed of materials encouraging tissue in-growth.

5. The intrauterine device according to claim 1, wherein the applied force is between 0.01 ft·lb and 0.025 ft·lb.

6. An intrauterine device for applying pressure to walls of a uterine cavity, the intrauterine device comprising:
a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;
a first plug member secured at the second end of the first leg and a second plug member secured at the first end of the second leg, the first and second prig members being shaped and dimensioned for bearing against the walls of the uterine cavity as the elongated member spreads outwardly with the first end and the second end moving apart;
wherein the first plug member and the second plug member are composed of bioresorbable materials.

7. The intrauterine device according to claim 1, wherein the resilient body includes a first extension arm extending from the second end of the first leg and a second extension arm extending from the second end of the second leg.

8. The intrauterine device according to claim 7, wherein the first extension arm is resiliently biased and the second extension arm is resiliently biased.

9. The intrauterine device according to claim 7, wherein the first extension arm includes a first end coupled to the second end of the first leg and the second extension arm includes a first end coupled to the second end of the second leg.

10. The intrauterine device according to claim 6, wherein the first plug member and the second plug member are composed of materials encouraging tissue in-growth.

11. An intrauterine device for applying pressure to walls of a uterine cavity, the intrauterine device comprising:
a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;
a first plug member secured at the second end of the first leg and a second plug member secured at the first end of the second leg, the first and second prig members being shaped and dimensioned for bearing against the walls of the uterine cavity as the elongated member spreads outwardly with the first end and the second end moving apart;
wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg; and wherein a third plug member is secured to the second end of the first extension arm and a fourth plug member is secured to the second end of the second extension arm.

12. An intrauterine device for applying pressure to walls of a uterine cavity, the intrauterine device comprising:
a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;
a first plug member secured at the second end of the first leg and a second plug member secured at the first end of the second leg, the first and second prig members being shaped and dimensioned for bearing against the walls of the uterine cavity as the elongated member spreads outwardly with the first end and the second end moving apart;
wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg; and wherein the first extension arm is substantially C-shaped and the second end extension arm is substantially C-shaped, wherein a concave portion of the first extension arm faces a concave portion of the second extension arm.

13. A method for preventing conception within the uterine cavity comprising the following steps:
delivering an intrauterine device into a uterine cavity, the intrauterine device including an elongated member with a first end and second end, and a first plug member secured at the first end of the elongated member and a second plug member secured at the second end of the elongated member;
causing the intrauterine device to apply pressure within the uterine cavity in a manner that will alter the shape of the uterine cavity over time thus preventing conception;
wherein the first and second plug members respectively apply a force of at least 0.01 ft·lb to lateral walls of the uterine cavity.

14. The method according to claim 13, further including the step of causing irritation and encouraging tissue in-growth into the first plug member and the second plug member.

15. The method according to claim 13, wherein the force applied is between 0.01 ft·lb and 0.025 ft·lb.

16. The method according to claim 13, wherein the first plug member and the second plug member are composed of materials encouraging tissue in-growth.

17. The method according to claim 13, wherein the resilient body includes a first extension arm extending from the second end of the first leg and a second extension arm extending from the second end of the second leg.

18. The method according to claim 17, wherein the first extension arm is resiliently biased and the second extension arm is resiliently biased.

19. The method according to claim 17, wherein the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity.

20. The method according to claim 13, wherein the first and second plug members are positioned on the lateral walls of the uterine cavity, below respective orifices of fallopian tubes.

21. A method for preventing conception within a uterine cavity, comprising the following steps:
   delivering an intrauterine device into the uterine cavity, the intrauterine device including an elongated member with a first end and second end, and a first plug member secured at the first end of the elongated member and a second plug member secured at the second end of the elongated member;
   causing the intrauterine device to apply pressure within the uterine cavity in a manner that will alter the shape of the uterine cavity over time thus preventing conception;
   wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension at is shaped and dimensioned for applying pressure to the upper wall of intrauterine cavity where a third plug member is secured to the second end of the first extension arm and a fourth plug member is secured to the second end of the second extension arm.

22. A method for preventing conception within a uterine cavity, comprising the following steps:
   delivering an intrauterine device into the uterine cavity, the intrauterine device including an elongated member with a first end and second end, and a first plug member secured at the first end of the elongated member and a second plug member secured at the second end of the elongated member;
   causing the intrauterine device to apply pressure within the uterine cavity in a manner that will alter the shape of the uterine cavity over time thus preventing conception;
   wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension at is shaped and dimensioned for applying pressure to the upper wall of intrauterine cavity, and wherein the first extension arm is substantially C-shaped and the second end extension arm is substantially C-shaped, wherein a concave portion of the first extension arm faces a concave portion of the second extension arm.

23. A method for delivering an intrauterine device, comprising:
   advancing the intrauterine device into the uterine cavity, the intrauterine device including an elongated member with a first end and second end, and a first plug member secured at the first end of the elongated member and a second plug member secured at the second end of the elongated member;
   releasing the intrauterine device, release resulting in (a) the first and second plug members first moving outwardly due to stored outward bias in the elongated member, (b) the first and second plug members then moving upwardly within the uterine cavity, (c) the first and second plug members then moving into contact with respective opposed walls of the uterine cavity and (d) the first and second plug members applying pressure to respective opposed walls of the uterine cavity to prevent conception within the uterine cavity;
   wherein the resilient body includes a first extension arm extending from the second end of the first leg and a second extension arm extending from the second end of the second leg; the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity, and wherein a third plug member is secured to the second end of the first extension arm and a fourth plug member is secured to the second end of the second extension arm.

24. The method according to claim 23, wherein the resilient body includes a first extension arm extending from the second end of the first leg and a second extension arm extending from the second end of the second leg.

25. The method according to claim 24, wherein the first extension arm is resiliently biased and the second extension arm is resiliently biased.

26. The method according to claim 24, wherein the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity.

27. The method according to claim 23, wherein the first and second plug members are positioned on the lateral walls of the uterine cavity, below respective orifices of fallopian tubes.

28. A method for delivering an intrauterine device, comprising:
   advancing the intrauterine device into the uterine cavity, the intrauterine device including an elongated member with a first end and second end, and a first plug member secured at the first end of the elongated member and a second plug member secured at the second end of the elongated member;

releasing the intrauterine device, release resulting in (a) the first and second plug members first moving outwardly due to stored outward bias in the elongated member, (b) the first and second plug members then moving upwardly within the uterine cavity, (c) the first and second plug members then moving into contact with respective opposed walls of the uterine cavity and (d) the first and second plug members applying pressure to respective opposed walls of the uterine cavity to prevent conception within the uterine cavity;

wherein the resilient body includes a first extension arm extending from the second end of the first leg and a second extension arm extending from the second end of the second leg; the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity, and wherein the first extension arm is substantially C-shaped and the second end extension arm is substantially C-shaped, wherein a concave portion of the first extension arm faces a concave portion of the second extension arm.

29. A method for delivering an intrauterine device, comprising:

advancing the intrauterine device into the uterine cavity, the intrauterine device including an elongated member with a first end and second end, and a first plug member secured at the first end of the elongated member and a second plug member secured to the second end of the elongated member;

releasing the intrauterine device, release resulting in (a) the first and second plug members first moving outwardly due to stored outward bias in the elongated member, (b) the first and second plug members then moving upwardly within the uterine cavity, (c) the first and second plug members then moving into contact with respective opposed walls of the uterine cavity and (d) the first and second plug members applying pressure of at least 0.01 ft·lb to respective opposed walls of the uterine cavity to prevent conception within the uterine cavity; wherein the plug members are impregnated with medicine.

30. A method for preventing conception within uterine cavity, comprising the following steps:

delivering an intrauterine device into the uterine cavity for positioning between lateral walls of the uterine cavity, the intrauterine device including an elongated member with a first end and second end, and a first plug member secured at the first end of the elongated member and a second plug member secured at the second end of the elongated member;

causing the intrauterine device to expand within the uterine cavity;

wherein the first and second plug members respectively apply a force of at least 0.01 ft·lb to the lateral walls of the uterine cavity.

31. The method according to claim 30, wherein the force applied is between approximately 0.01 ft.lb and 0.025 ft.lb.

32. The method according to claim 30, wherein the resilient body includes a first extension arm extending from the second end of the first leg and a second extension arm extending from the second end of the second leg.

33. The method according to claim 32, wherein the first extension arm is resiliently biased and the second extension arm is resiliently biased.

34. The method according to claim 32, wherein the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity.

35. The method according to claim 34, wherein a third plug member is secured to the second end of the first extension arm and a fourth plug member is secured to the second end of the second extension arm.

36. The method according to claim 30, wherein the first and second plug members are positioned on the lateral walls of the uterine cavity, below respective orifices of fallopian tubes.

37. A method for preventing conception within a uterine cavity, comprising the following steps:

delivering an intrauterine device into the uterine cavity for positioning between, lateral walls of the uterine cavity, the intrauterine device including an elongated member with a first end and second end, and a first plug member secured at the first end of the elongated member and a second plug member secured at the second end of the elongated member;

causing the intrauterine device to expand within the uterine cavity such that a distance between the first plug member and the second plug member is greater than the distance between opposed lateral walls of the uterine cavity;

wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity, wherein a third plug member is secured to the second end of the first extension arm and a fourth plug member is secured to the second end of the second extension arm, and wherein the first extension arm is substantially C-shaped and the second end extension arm is substantially C-shaped, wherein a concave portion of the first extension arm faces a concave portion of the second extension arm.

38. A method for preventing conception within a uterine cavity, comprising the following steps:

delivering an intrauterine device into the uterine cavity for positioning between lateral walls of the uterine cavity, the intrauterine device including an elongated member with a first end and second end, and a first plug member secured at the first end of the elongated member and a second plug member secured at the second end of the elongated member;

causing the intrauterine device to expand within the uterine cavity, so as to apply a force of at least 0.01 ft.lb to the lateral walls of the uterine cavity;

wherein the plug members are impregnated with medicine.

* * * * *

UNITED STATES PATENT AND TRADEMARK OFFICE
CERTIFICATE OF CORRECTION

PATENT NO. : 8,662,081 B2
APPLICATION NO. : 12/856876
DATED : March 4, 2014
INVENTOR(S) : Michael G. Tal et al.

Page 1 of 3

It is certified that error appears in the above-identified patent and that said Letters Patent is hereby corrected as shown below:

In the Claims:

Column 19, line 25, cancel the text beginning with "6. An intrauterine device" to and ending "bioresorbable materials", and insert the following claim:

--6. An intrauterine device for applying pressure to walls of a uterine cavity, the intrauterine device comprising:
a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;
a first plug member secured at the second end of the first leg and a second plug member secured at the first end of the second leg, the first and second plug members being shaped and dimensioned for bearing against the walls of the uterine cavity as the elongated member spreads outwardly with the first end and the second end moving apart;
wherein the first plug member and the second plug member are composed of bioresorbable materials.--

Column 19, line 59 through Column 20, line 20, cancel the text beginning with "11. An intrauterine device" to and ending "second extension arm", and insert the following claim:

--11. An intrauterine device for applying pressure to walls of a uterine cavity, the intrauterine device comprising:
a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;
a first plug member secured at the second end of the first leg and a second plug member Signed and Sealed this
Thirteenth Day of May, 2014

Michelle K. Lee
*Deputy Director of the United States Patent and Trademark Office* secured at the first end of the second leg, the first and second plug members being shaped and dimensioned for bearing against the walls of the uterine cavity as the elongated member spreads outwardly with the first end and the second end moving apart;

wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg; and wherein a third plug member is secured to the second end of the first extension arm and a fourth plug member is secured to the second end of the second extension arm.--

Column 20, line 21, cancel the text beginning with "12. An intrauterine device" to and ending "second extension arm", and insert the following claim:

--12. An intrauterine device for applying pressure to walls of a uterine cavity, the intrauterine device comprising:

a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;

a first plug member secured at the second end of the first leg and a second plug member secured at the first end of the second leg, the first and second plug members being shaped and dimensioned for bearing against the walls of the uterine cavity as the elongated member spreads outwardly with the first end and the second end moving apart;

wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg; and wherein the first extension arm is substantially C-shaped and the second end extension arm is substantially C-shaped, wherein a concave portion of the first extension arm faces a concave portion of the second extension arm.--

Column 21, line 25, cancel the text beginning with "21. A method for" to and ending "second extension arm", and insert the following claim:

--21. A method for preventing conception within a uterine cavity, comprising the following steps:

delivering an intrauterine device into the uterine cavity, the intrauterine device including an elongated member with a first end and second end, and a first plug member secured at the first end of the elongated member and a second plug member secured at the second end of the elongated member;

causing the intrauterine device to apply pressure within the uterine cavity in a manner that will alter the shape of the uterine cavity over time thus preventing conception;

wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying

CERTIFICATE OF CORRECTION (continued)
U.S. Pat. No. 8,662,081 B2 pressure to the upper wall of intrauterine cavity where a third plug member is secured to the second end of the first extension arm and a fourth plug member is secured to the second end of the second extension arm.--

Column 21, line 51 through Column 22, line 10, cancel the text beginning with "22. A method for" to and ending "second extension arm", and insert the following claim:

--22. A method for preventing conception within a uterine cavity, comprising the following steps:
  delivering an intrauterine device into the uterine cavity, the intrauterine device including an elongated member with a first end and second end, and a first plug member secured at the first end of the elongated member and a second plug member secured at the second end of the elongated member;
  causing the intrauterine device to apply pressure within the uterine cavity in a manner that will alter the shape of the uterine cavity over time thus preventing conception;
  wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of intrauterine cavity, and wherein the first extension arm is substantially C-shaped and the second end extension arm is substantially C-shaped, wherein a concave portion of the first extension arm faces a concave portion of the second extension arm.--

Column 24, line 23, cancel the text beginning with "37. A method for" to and ending "second extension arm", and insert the following claim:

--37. A method for preventing conception within a uterine cavity, comprising the following steps:
  delivering an intrauterine device into the uterine cavity for positioning between lateral walls of the uterine cavity, the intrauterine device including an elongated member with a first end and second end, and a first plug member secured at the first end of the elongated member and a second plug member secured at the second end of the elongated member;
  causing the intrauterine device to expand within the uterine cavity such that a distance between the first plug member and the second plug member is greater than the distance between opposed lateral walls of the uterine cavity;
  wherein the resilient body includes a first extension arm extending from the second end of the first leg and a second extension arm extending from the second end of the second leg, the first extension arm includes a first end coupled to the second end of the first leg and the second extension arm includes a first end coupled to the second end of the second leg, and wherein the second end of the first extension arm is shaped and dimensioned for applying pressure to an upper wall of the uterine cavity and the second end of the second extension arm is shaped and dimensioned for applying pressure to the upper wall of the uterine cavity, wherein a third plug member is secured to the second end of the first extension arm and a fourth plug member is secured to the second end of the second extension arm, and wherein the first extension arm is substantially C-shaped and the second end extension arm is substantially C-shaped, wherein a concave portion of the first extension arm faces a concave portion of the second extension arm.--

UNITED STATES PATENT AND TRADEMARK OFFICE
CERTIFICATE OF CORRECTION

| | | |
|---|---|---|
| PATENT NO. | : 8,662,081 B2 | Page 1 of 1 |
| APPLICATION NO. | : 12/856876 | |
| DATED | : March 4, 2014 | |
| INVENTOR(S) | : Michael G. Tal et al. | |

It is certified that error appears in the above-identified patent and that said Letters Patent is hereby corrected as shown below:

In the Claims:

Column 18, line 55 through Column 19, line 8, cancel the text beginning with "1. An intrauterine device" to and ending "the uterine cavity", and insert the following claim:

--1. An intrauterine device for applying pressure to lateral walls of a uterine cavity, the intrauterine device comprising:

a resilient body including an elongated member having a first end and a second end which are resiliently biased away from each other, the first end of the elongated member including a first leg having a first end and a second end, and the second end of the elongated member including a second leg having a first end and a second end, wherein a connection member is positioned between the first end of the first leg and the first end of the second leg;

a first plug member secured at the second end of the first leg and a second plug member secured at the second end of the second leg, the first and second plug members being shaped and dimensioned for bearing against the walls of the uterine cavity as the elongated member spreads outwardly with the first end and the second end moving apart;

wherein the first and second plug members respectively apply a force of at least 0.01 ftlb to the lateral walls of the uterine cavity.--

Signed and Sealed this
Seventeenth Day of March, 2015

Michelle K. Lee
*Director of the United States Patent and Trademark Office*